US007211415B2

(12) United States Patent
Rieping et al.

(10) Patent No.: US 7,211,415 B2
(45) Date of Patent: May 1, 2007

(54) ENTEROBACTERIACEAE STRAINS OVER-EXPRESSING THE YFID GENE FOR THE FERMENTATIVE PRODUCTION OF L-AMINO ACIDS

(75) Inventors: Mechthild Rieping, Bielefeld (DE); Mike Farwick, Essen (DE)

(73) Assignee: Degussa AG, Düsseldorf (DE)

( * ) Notice: Subject to any disclaimer, the term of this patent is extended or adjusted under 35 U.S.C. 154(b) by 203 days.

(21) Appl. No.: 10/817,431

(22) Filed: Apr. 5, 2004

(65) Prior Publication Data
US 2004/0235122 A1  Nov. 25, 2004

(30) Foreign Application Priority Data
Apr. 9, 2003 (DE) .................. 103 16 109

(51) Int. Cl.
C12P 13/04 (2006.01)
C12P 13/08 (2006.01)
C12N 1/20 (2006.01)
C12N 1/21 (2006.01)
C12N 15/74 (2006.01)
C12Q 1/68 (2006.01)
C07H 21/02 (2006.01)

(52) U.S. Cl. .................. 435/106; 435/115; 435/69.1; 435/116; 435/252.3; 435/488; 435/113; 435/252.33; 435/6; 536/23.1

(58) Field of Classification Search ............ 435/252.3, 435/106
See application file for complete search history.

(56) References Cited

U.S. PATENT DOCUMENTS 4,278,765 A   7/1981 Debabov et al. ............ 435/172

FOREIGN PATENT DOCUMENTS

| DE | 101 32 946 A1 | 7/2001 |
|---|---|---|
| DE | 101 35 053 A1 | 7/2001 |
| EP | 0 271 838 A2 | 6/1988 |
| EP | 0 994 190 A2 | 4/2000 |
| EP | 1 013 765 A1 | 6/2000 |
| EP | 1 149 911 A2 | 10/2001 |
| WO | WO 99/18228 | 4/1999 |
| WO | WO 99/53035 | 10/1999 |
| WO | WO 01/05939 A1 | 1/2001 |
| WO | WO 01/92545 A1 | 12/2001 |
| WO | WO 02/06459 A1 | 1/2002 |
| WO | WO 02/29080 A2 | 4/2002 |
| WO | WO 02/36797 A2 | 5/2002 |
| WO | WO 02/064808 A1 | 8/2002 |
| WO | WO 02/077183 | 10/2002 |
| WO | WO 02/081698 A2 | 10/2002 |
| WO | WO 02/081721 A2 | 10/2002 |
| WO | WO 02/081722 A2 | 10/2002 |
| WO | WO 03/004598 A2 | 1/2003 |
| WO | WO 03/004663 A2 | 1/2003 |
| WO | WO 03/004664 A2 | 1/2003 |
| WO | WO 03/004665 A2 | 1/2003 |
| WO | WO 03/004669 A2 | 1/2003 |
| WO | WO 03/004670 A2 | 1/2003 |
| WO | WO 03/004671 A2 | 1/2003 |
| WO | WO 03/004674 A2 | 1/2003 |
| WO | WO 03/006666 A2 | 1/2003 |
| WO | WO 03/008603 A2 | 1/2003 |
| WO | WO 03/008604 A2 | 1/2003 |
| WO | WO 03/008605 A2 | 1/2003 |
| WO | WO 03/008606 A2 | 1/2003 |
| WO | WO 03/008607 A2 | 1/2003 |
| WO | WO 03/008608 A2 | 1/2003 |
| WO | WO 03/008609 A2 | 1/2003 |
| WO | WO 03/008610 A2 | 1/2003 |
| WO | WO 03/008612 A2 | 1/2003 |
| WO | WO 03/008613 A2 | 1/2003 |
| WO | WO 03/008614 A2 | 1/2003 |
| WO | WO 03/008615 A2 | 1/2003 |
| WO | WO 03/038106 A2 | 5/2003 |
| WO | WO 03/076635 A1 | 9/2003 |
| WO | WO 03/076637 | 9/2003 |

OTHER PUBLICATIONS

Andrews, et al., "Cloning, Sequencing, and Mapping of the Bacterioferritin Gene (*bfr*) of *Escherichia coli* K-12," *J. Bacteriol.* 171:3940-3947 (1989).
Blankenhorn, et al., "Acid- and Base-Induced Proteins during Aerobic and Anaerobic Growth of *Escherichia coli* Revealed by Two-Dimensional Gel Electrophoresis," *J. Bacteriol.* 181:2209-2216 (1999).
Blattner, et al., "The Complete Genome Sequence of *Escherichia coli* K-12," *Science* 277:1453-1462 (1997).
Boos, et al., "Maltose/Maltodextrin System of *Escherichia coli*: Transport, Metabolism, and Regulation," *Microbiol. Mol. Biol. Rev.* 62:204-229 (1998).
Brune, et al., "Cloning and Sequencing of the Adenylate Kinase Gene (*adk*) of *Escherichia coli*," *Nucleic Acids Res.* 13:7139-7151 (1985).
Carrier, et al., "Library of Synthetic 5' Secondary Structures to Manipulate mRNA Stability in *Escherichia coli*," *Biotechnol. Prog.* 15:58-64 (1999).
Clarke, et al., "Nucleotide Sequence of the *pntA* and *pntB* Genes Encoding the Pyridine Nucleotide Transhydrogenase of *Escherichia coli*," *Eur. J. Biochem.* 158:647-653 (1986).

(Continued)

Primary Examiner—Rebecca E. Prouty
Assistant Examiner—Iqbal Chowdhury
(74) Attorney, Agent, or Firm—Michael A. Sanzo; Law Office of Michael A. Sanzo, LLC

(57) ABSTRACT

The present invention relates to a process for the production of L-amino acids by fermentation of recombinant microorganisms of the Enterobacteriaceae family, wherein
a) the yfiD ORF and/or the pflB gene or nucleotide sequences coding for the gene products are overexpressed in the microorganisms producing the desired L-amino acid, and the microorganisms are cultured in a medium under conditions in which the desired L-amino acid is enriched in the medium or in the cells; and
b) the desired L-amino acid is isolated, in a manner such that constituents of the fermentation broth and/or the biomass in its entirety or in portions (>0 to 100%) either remain in the isolated product or are completely removed.

15 Claims, 2 Drawing Sheets

OTHER PUBLICATIONS

Cole, et al., "The Nucleotide Sequence of the *malT* Gene Encoding the Positive Regulator of *Escherichia coli* Maltose Regulon," *Gene* 42:201-208 (1986).

Danot, "A Complex Signaling Module Governs the Activity of MalT, the Prototype of an Emerging Transactivator Family," *Proc. Natl. Acad. Sci. USA* 98:435-440 (2001).

DiRusso, "Nucleotide Sequence of the *fadR* Gene, a Multifunctional Regulator of Fatty Acid Metabolism in *Escherichia coli,*" *Nucleic Acids Res.* 16:7995-8009 (1988).

Enos-Berlage, et al., "Complex Metabolic Phenotypes Caused by a Mutation in *yigF*, Encoding a Member of the Highly Conserved YER057c/YjgF Family of Proteins," *J. Bacteriol.* 180:6519-6528 (1998).

Fountoulakis, et al., "Enrichment of Low Abundance Proteins of *Escherichia coli* by Hydroxyapatite Chromatography," *Electrophoresis* 20:2181-2195 (1999).

Franch, et al., "U-Turns and Regulatory RNAs," *Curr. Opin. Microbiol.* 3:159-164 (2000).

Garrido-Pertierra, "Isolation and Properties of *Salmonella typhimurium* Mutants Defective in Enolase," *Revista Española de Fisiologia* 36:33-40 (1980).

Gulick, et al., "Evolution of Enzymatic Activities in the Enolase Superfamily: Crystal Structures of the L-Ala-D/L-Glu Epimerases from *Escherichia coli* and *Bacillus subtilis,*" *Biochemistry* 40:15716-15724 (2001).

Heim, et al., "Cloning an *Escherichia coli* Gene Encoding a Protein Remarkably Similar to Mammalian Aldehyde Dehydrogenases," *Gene* 99:15-23 (1991).

Hofnung, Divergent Operons and the Genetic Structure of the Maltose B Region in *Escherichia coli* K12, *Genetics* 76:169-184 (1974).

Hogg, et al., "Nucleotide Sequence and Analysis of the *mgl* Operon of *Escherichia coli* K12," *Mol. Gen. Genet.* 229:453-459 (1991).

Jensen, et al., "Artificial Promoters for Metabolic Optimization," *Biotechnol. Bioeng.* 58:191-195 (1998).

Kaga, et al., "Rnase G-Dependent Degradation of the *eno* mRNA Encoding a Clycolysis Enzyme Enolase in *Escherichia coli,*" *Biosci. Biotechnol. Biochem.* 66:2216-2220 (2002).

Kirkpatrick, et al., "Acetate and Formate Stress: Opposite Responses in the Proteome of *Escherichia coli,*" *J. Bacteriol.* 183:6466-6477 (2001).

Klein, et al., "Cloning, Nucleotide Sequence, and Functional Expression of the *Escherichia coli* Enolase (*eno*) Gene in a Temperature-Sensitive *eno* Mutant Strain," *J. Seq. Mapping* 6:351-355 (1996).

Knappe, et al., "A Radical-Chemical Route to Acetyl-CoA: The Anaerobically Induced Pyruvate Formate-Lyase System of *Escherichia coli,*" *FEMS Microbiol. Rev.* 75:383-398 (1990).

Komatsubara, et al., "Transductional Construction of a Threonine-Producing Strain of *Serratia marcescens,*" *Appl. Environ. Microbiol.* 38:1045-1051 (1979).

Landgraf, et al., "The Role of H-NS is One Carbon Metabolism," *Biochimie* 76:1063-1070 (1994).

Lee, et al., "Global Analysis of Transcriptomes and Proteomes of a Parent Strain and an L-Threonine-Overproducing Mutant Strain," *J. Bacteriol.* 185:5442-5451 (2003).

Macpherson, et al., "Identification of the GalP Galactose Transport Protein of *Escherichia coli,*" *J. Biol. Chem.* 258:4390-4396 (1983).

Martin, et al., "Forskolin Specifically Inhibits the Bacterial Galactose-$H^+$ Transport Protein, GalP," *J. Biol. Chem.* 268:24870-24877 (1994).

Masuda, et al., "Improvement of Nitrogen Supply for L-Threonine Production by a Recombinant Strain of *Serratia marcescens,*" *Appl. Biochem. Biotechnol.* 37:255-265 (1992).

McPherson, et al., "Complete Nucleotide Sequence of the *Escherichia coli gdhA* Gene," *Nucleic Acids Res.* 11:5257-5267 (1983).

Meyer, et al., Molecular Characterization of Glucokinase from *Escherichia coli* K-12, *J. Bacteriol.* 179:1298-1306 (1997).

Missiakas, et al., "Modulation of the *Escherichia coli* $o^E$ (RpoE) Heat-Shock Transcription-Factor Activity by the RseA, RseB and RseC Proteins," *Mol. Microbiol.* 24:355-371 (1997).

Nagelkerke, et al., "2-Deoxygalactose, a Specific Substrate of the *Salmonella typhimurium* Galactose Permease: Its Use for the Isolation of *galP* Mutants," *J. Bacteriol.* 133:607-613 (1978).

Niersbach, et al., "Cloning and Nucleotide Sequence of the *Escherichia coli* K-12 *ppsA* Gene, Encoding PEP Synthase," *Mol. Gen. Genet.* 231:332-336 (1992).

Parsons, et al., "Solution Structure and Functional Ligand Screening of H10719, a Highly Conserved Protein from Bacteria to Humans in the YjgF/YER057c/UK114 Family," *Biochemistry* 42:80-89 (2003).

Postma, "Galactose Transport in *Salmonella typhimurium,*" *J. Bacteriol.* 129:630-639 (1977).

Qiu, et al., "The *Escherichia coli polB* Locus Is Identical to *dinA*, the Structural Gene for DNA Polymerase II," *J. Biol. Chem.* 272:8611-8617 (1997).

Raibaud, et al., "Maltotriose Is the Inducer of the Maltose Regulon of *Escherichia coli,*" *J. Bacteriol.* 169:3059-3061 (1987).

Raibaud, et al., "Essential and Nonessential Sequences in *malPp*, a Positively Controlled Promoter in *Escherichia coli,*" *J. Bacteriol.* 161:1201-1208 (1985).

Ravnikar, et al., "Structural and Functional Analysis of a Cloned Segment of *Escherichia coli* DNA That Specifies Proteins of a $C_4$ Pathway of Serine Biosynthesis," *J. Bacteriol.* 169:4716-4721 (1987).

Reyes, et al., "Overproduction of MalK Protein Prevents Expression of the *Escherichia coli mal* Regulon," *J. Bacteriol.* 170:4598-4602 (1988).

Richet, et al., "MalT, the Regulatory Protein of the *Escherichia coli* Maltose System, In an ATP-Dependent Transcriptional Activator," *EMBO J.* 8:981-987 (1989).

Rödel, et al., "Primary Structures of *Escherichia coli* Pyruvate Formate-Lyase and Pyruvate-Formatre-Lyase-Activating Enzyme Deduced from the DNA Nucleotide Sequences," *Eur. J. Biochem.* 177:153-158 (1988).

Romeo, et al., "Identification and Molecular Characterizatrion of *csrA*, a Pleiotropic Gene from *Escherichia coli* That Affects Glycogen Biosynthesis, Gluconeogenesis, Cell Size, and Surface Properties," *J. Bacteriol.* 175:4744-4755 (1993).

Sabe, et al., "Molecular Cloning of the Phosphoenolpyruvate Carboxylase Gene, *ppc*, of *Escherichia coli,*" *Gene* 31:279-283 (1984).

Schlegel, et al., "Network Regulation of the *Escherichia coli* Maltose System," *J. Mol. Microbiol. Biotechnol.* 4:301-307 (2002).

Schmitz, et al., "Reduced Transaminase B (IlvE) Activity Caused by the Lack of *yigF* Is Dependent on the Status of Threonine Deaminase (IlvA) in *Salmonella enterica* Serovar Typhimurium," *J. Bacteriol.* 186:803-810 (2004).

Schreiber, et al., "A New Mechanism for the Control of Prokaryotic Transcriptional Regulator: Antagonistic Binding of Positive and Negative Effectors," *Mol. Microbiol.* 35:765-776 (2000).

Spring, et al., "The Purification and Characterization of *Escherichia coli* Enolase," *J. Biol. Chem.* 246:6797-6802 (1971).

Stephens, et al., "The Pyruvate Dehydrogenase Complex of *Escherichia coli* K-12—Nucleotide Sequence Encoding the Pyruvate Dehydrogenase Component," *Eur. J. Biochem.* 133:155-162 (1983).

Stephens, et al., "The Pyruvate Dehydrogenase Complex of *Escherichia coli* K12—Nucleotide Sequence Encoding the Dihydrolipoamide Acetyltransferase Component," *Eur. J. Biochem.* 133:481-489 (1983).

Stephens, et al., "Nucleotide Sequence of the Lipoamide Dehydrogenase Gene of *Escherichia coli* K12," *Eur. J. Biochem.* 135:519-527 (1983).

Sugita, et al., "Cloning and Characterization of the Mutated Threonine Operon ($thrA_1 5A_2 5BC$) of *Serratia marcescens,*" *Gene* 57:151-158 (1987).

Sunnarborg, et al., "Regulation of the Glyoxylate Bypass Operon: Cloning and Characterization of *iclR,*" *J. Bacteriol.* 172:2642-2649 (1990).

Suzuki, et al., "Mapping, Cloning, and DNA Sequencing of *pepB* Which Encodes Peptidase B of *Escherichia coli* K-12," *J. Ferment. Bioeng.* 82:392-397 (1996).

Thorsness, et al., "Inactivation of Isocitrate Dehydrogenase by Phosphorylation Is Mediated by the Negative Charge of the Phosphate," *J. Biol. Chem.* 262:10422-10425 (1987).

Valle, et al., "Nucleotide Sequence of the Promoter and Amino-Terminal Coding Region of the Glutamate Dehydrogenase Structural Gene of *Escherichia coli*," *Gene* 23:199-209 (1983).

Venter, et al., "Molecular Dissection of Membrane-Transport Proteins: Mass Spectrometry and Sequence Determination of the Galactose-$H^+$ Symport Protein, GalP, of *Escherichia coli* and Quantitative Assay of the Incorporation of [$ring$-$2^{13}C$]histidine and $^{15}NH_3$," *Biochem J.* 363:243-252 (2002).

Vidal-Ingigliardi, et al., "A Small C-Terminal Region of the *Escherichia coli* MalT Protein Contains the DNA- Binding Domain," *J. Biol. Chem.* 268:24527-24530 (1993).

Vogel, et al., "Cloning and Sequenc of the *mdh* Structural Gene of *Escherichia coli* Coding for Malate Dehydrogenase," *Arch. Microbiol.* 149:36-42 (1987).

Volz, "A Test Case for Structure-Based Functional Assignment: The 1.2 Å Crystal Structure of the yjgF Gene Product form *Escherichia coli*," *Protein Science* 8:2428-2437 (1999).

Wagner, et al., "The Free Radical in Pyruvate Formate-Lyase Is Located on Glycine-734," *Proc. Natl. Acad. Sci. USA* 89:996-1000 (1992).

Walmsley, et al., "8-Anilino-1-Napthalenesulfonate Is a Fluorescent Probe of Conformational Changes in the D-Galactose-$H^+$ Simport Protein of *Escherichia coli*," *J. Biol. Chem.* 269:17009-17019 (1994).

Walton, et al., "Nucleotide Sequence of the *Escherichia coli* Uridine Phosphorylase (*udp*) Gene," *Nucleic Acids Res.* 17:6741 (1989).

Wasinger, et al., "Small Genes/Gene-Products in *Escherichia coli* K-12," *FEMS Microbiol. Lett.* 169:375-382 (1998).

Wente, et al., "Different Amino Acid Substitutions at the Same Position in the Nucleotide-Binding Site of Aspartate Transcarbamoylase Have Diverse Effects on the Allosteric Properties of the Enzyme," *J. Biol. Chem.* 266:20833-20839 (1991).

Wong, et al., "Transcription of *pfl* Is Regulatred by Anaerobiosis, Calabolite Repression, Pyruvate, and *oxrA*: *pfl*::MU dA Operon Fusions of *Salmonella typhimurium*," *J. Bacteriol.* 171:4900-4905 (1989).

Wyborn, et al., "Expression of the *Escherichia coli yfiD* Gene Responds to Intracellular pH and Reduces the Accumulation of Acidic Metabolic End Products," *Microbiology* 148:1015-1026 (2002).

Yano, et al., "Directed Evolution of an Aspartate Aminotransferase with New Substrate Specificities," *Proc. Natl. Acad. Sci. USA* 95:5511-5515 (1998).

Yoshida, et al., "Physical Map Location of a Set of *Escherichia coli* Genes (*hde*) Whose Expression Is Affected by the Nucleoid Protein H-NS," *J. Bacteriol.* 175:7747-7748 (1993).

Abstract of Reference B1, WO 99/18228.

Abstract of Reference B3, WO 01/05939.

Abstract of Reference B39, DE 101 32 946.

Abstract of Reference B40, DE 101 35 053.

Hermann, et al., "Improved L-Threonine Production with *Escherichia coli*," *Proceedings of European Congress Biotechnology*, XX, XX, Aug. 24, 2003, p. 85.

Lehninger, et al., *Principles of Biochemistry*, Worth Publishers, 2nd Edition, pp. 697-715 (1997).

McClelland, et al., "Complete Genome Sequence of *Salmonella enterica* Serovar Typhimurium LT2," *Nature* 413:852-856 (2001).

Sofia, et al., "Analysis of the *Escherichia coli* Genome. V. DNA Sequence of the Region from 76.0 to 81.5 Minutes," *Nucleic Acids Res.* 22(13):2576-2586 (1994).

Database UniProt 'Online!', Jul. 1, 1898, "Putative Glycosyl Transferase yibD (EC 2.-.-.-)," XP-002324637.

Database EMBL 'Online!', Jun. 2, 1994, "*E. coli* Chromosomal Region from 76.0 to 81.5 Minutes," XP-00234368.

Database EMBL 'Online!', Oct. 29, 2001, "*Salmonella tphyimurium* LT2, Section 176 of 220 of the Complete Genome," XP-002324369.

ENTEROBACTERIACEAE STRAINS OVER-EXPRESSING THE YFID GENE FOR THE FERMENTATIVE PRODUCTION OF L-AMINO ACIDS

CROSS REFERENCE TO RELATED APPLICATIONS

The present application claims priority to German application 103 16 109.0, filed on Apr. 9, 2003, which is incorporated in its entirety herein by reference.

FIELD OF THE INVENTION

This invention relates to a process for the fermentative production of L-amino acids, particularly L-threonine, using strains of the Enterobacteriaceae family in which the open reading frame (ORF) having the designation yfiD and/or the pflB gene is/are enhanced.

BACKGROUND OF THE INVENTION

L-amino acids such as L-threonine are used in human medicine, in the pharmaceutical industry, in the food industry and, very particularly, in animal nutrition. It is known that L-amino acids can be prepared by the fermentation of strains of Enterobacteriaceae, especially *Escherichia coli* (*E. coli*) and *Serratia marcescens*. As a result of the great importance of these amino acids, efforts are constantly made to improve production methods. Process improvements may relate to fermentation engineering measures, e.g., methods of stirring and supplying oxygen, or to the composition of the nutrient media, e.g., the sugar concentration present during fermentation. Alternatively, improvements may relate to the way in which product is purified, e.g., ion-exchange chromatography, or to the intrinsic performance characteristics of the microorganism itself.

Methods of mutagenesis, selection and mutant choice are often used to improve the performance characteristics of microorganisms. In this way, strains are obtained that are resistant to antimetabolites such as the threonine analog α-amino-β-hydroxyvaleric acid (AHV) or that are auxotrophic for regulatorily important metabolites and which produce L-amino acids such as L-threonine. For some time now, methods of recombinant DNA engineering have also been used for improving L-amino acid-producing strains of the Enterobacteriaceae family. This often involves amplifying individual amino acid biosynthesis genes and testing the effect of this amplification on production. A summary of information relating to the cellular biology and molecular biology of *Escherichia coli* and *Salmonella* can be found in Neidhardt (ed.): *Escherichia coli and Salmonella, Cellular and Molecular Biology*, 2$^{nd}$ edition, ASM Press, Washington, D.C., USA,(1996).

OBJECT OF THE INVENTION

The object of the present invention is to provide new measures for the improved fermentative production of L-amino acids and, in particular, L-threonine.

SUMMARY OF THE INVENTION

The invention provides a process for the fermentative production of L-amino acids using microorganisms from the Enterobacteriaceae family in which at least the yfiD open reading frame (ORF) and/or the pflB gene, or nucleotide sequence(s) or alleles coding for the products thereof, is/are overexpressed.

In its first aspect, the invention is directed to a process for the production of an L-amino acid product by fermenting a recombinant microorganism from the Enterobacteriaceae family (preferably from the genus *Escherichia, Erwinia, Providencia*, or *Serratia*) in a fermentation medium. The recombinant microorganism produces the desired L-amino acid and is characterized by increased activity of the yfiD ORF product and/or the pflB gene product.

Increased activity may be due to the overexpression of the yfiD ORF or pfl D gene endogenously present or due to the expression of another nucleotide sequence coding for the yfiD ORF product and/or the pflB gene product. One method for increasing the expression of polynucleotides is to increase copy number by at least 1. Increase in copy number can be achieved by integration of the gene or ORF into the chromosome of the microorganism or by means of an extra-chromosomally replicating vector. Alternatively, expression may be increased by mutating or replacing the promoter or ribosome binding site upstream of the yfiD ORF and/or the pflB gene. Preferably, recombinant engineering results in a concentration or activity of the yfiD gene product and/or of the pflB gene product (protein) that is increased by at least 10%, relative to the activity or concentration of the gene product in the initial strain.

After allowing the desired amino acid to become enriched in either the fermentation medium or in the microorganism itself, it is isolated to produce the L-amino acid product. Amino acids that may be produced using this process include L-asparagine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan L-threonine, L-homoserine and L-arginine. The most preferred of these is L-threonine. It is also preferred that some or all of the constituents of the fermentation broth and/or biomass from the microorganism undergoing fermentation remain in the final amino acid product.

The process described above may be carried out using a microorganism in which, in addition to enhanced activity of the yfiD ORF product and/or the pflB gene product, at least one gene in a biosynthesis pathway of the L-amino acid being produced is also overexpressed. Examples of specific genes that may be overexpressed include:

a) the thrABC operon coding for aspartate kinase, homoserine dehydrogenase, homoserine kinase and threonine synthase;
b) the pyc gene coding for pyruvate carboxylase;
c) the pps gene for phosphoenolpyruvate synthase;
d) the ppc gene coding for phosphoenolpyruvate carboxylase;
e) the genes pntA and pntB coding for transhydrogenase;
f) the rhtB gene imparting homoserine resistance;
g) the mqo gene coding for malate:quinone oxidoreductase;
h) the rhtC gene imparting threonine resistance;
i) the thrE gene coding for the threonine-export protein;
j) the gdhA gene coding for glutamate dehydrogenase;
k) the hns gene coding for the DNA binding protein HLP-II;
l) the pgm gene coding for phosphoglucomutase;
m) the fba gene coding for fructose biphosphate aldolase;
n) the ptsH gene coding for phosphohistidine protein hexose phosphotransferase;

o) the ptsI gene coding for enzyme I of the phosphotransferase system;
p) the crr gene coding for the glucose-specific IIA component;
q) the ptsG gene coding for the glucose-specific IIBC component;
r) the lrp gene coding for the regulator of the leucine regulon;
s) the csrA gene coding for the global regulator Csr;
t) the fadR gene coding for the regulator of the fad regulon;
u) the iclR gene coding for the regulator of central intermediary metabolism;
v) the mopB gene coding for the 10 kDa chaperon;
w) the ahpC gene coding for the small subunit of alkyl hydroperoxide reductase;
x) the ahpF gene coding for the large subunit of alkyl hydroperoxide reductase;
y) the cysK gene coding for cysteine synthase A;
z) the cysB gene coding for the regulator of the cys regulon;
aa) the cysJ gene coding for the flavoprotein of NADPH sulfite reductase;
bb) the cysI gene coding for the haemoprotein of NADPH sulfite reductase;
cc) the cysH gene coding for adenylyl sulfate reductase;
dd) the phoB gene coding for the positive regulator PhoB of the pho regulon;
ee) the phoR gene coding for the sensor protein of the pho regulon;
ff) the phoE gene coding for protein E of the outer cell membrane;
gg) the pykF gene coding for pyruvate kinase I, which is stimulated by fructose;
hh) the pfkB gene coding for 6-phosphofructokinase II;
ii) the malE gene coding for the periplasmic binding protein of maltose transport;
jj) the sodA gene coding for superoxide dismutase;
kk) the rseA gene coding for a membrane protein with anti-sigmaE activity;
ll) the rseC gene coding for a global regulator of the sigmaE factor;
mm) the sucA gene coding for the decarboxylase subunit of 2-ketoglutarate dehydrogenase;
nn) the sucB gene coding for the dihydrolipoyl transsuccinase E2 subunit of 2-ketoglutarate dehydrogenase;
oo) the sucC gene coding for the β-subunit of succinyl-CoA synthetase;
pp) the sucD gene coding for the α-subunit of succinyl-CoA synthetase;
qq) the adk gene coding for adenylate kinase;
rr) the hdeA gene coding for a periplasmic protein with chaperonin-type function;
ss) the hdeB gene coding for a periplasmic protein with chaperonin-type function;
tt) the icd gene coding for isocitrate dehydrogenase;
uu) the mglB gene coding for the periplasmic, galactose-binding transport protein;
vv) the lpd gene coding for dihydrolipoamide dehydrogenase;
ww) the aceE gene coding for the E1 component of the pyruvate-dehydrogenase complex;
xx) the aceF gene coding for the E2 component of the pyruvate-dehydrogenase complex;
yy) the pepB gene coding for aminopeptidase B;
zz) the aldH gene coding for aldehyde dehydrogenase;
aaa) the bfr gene coding for the iron-storage homoprotein;
bbb) the udp gene coding for uridine phosphorylase; and
ccc) the rseB gene coding for the regulator of sigmaE-factor activity.

Alternatively, a microorganism may be used in which, in addition to enhanced activity of the yfiD ORF product and/or the pflB gene product, the activity of the product of one or more additional genes is attenuated or eliminated or the expression of one or more additional genes or ORFs is diminished. Specific genes that may be attenuated by either being switched off or having their expression reduced, include:

a) the tdh gene coding for threonine dehydrogenase;
b) the mdh gene coding for malate dehydrogenase;
c) the open reading frame (ORF) yjfA;
d) the open reading frame (ORF) ytfP;
e) the pckA gene coding for phosphoenolpyruvate carboxykinase;
f) the poxB gene coding for pyruvate oxidase;
g) the aceA gene coding for isocitrate lyase;
h) the dgsA gene coding for the DgsA regulator of the phosphotransferase system;
i) the fruR gene coding for the fructose repressor;
j) the rpoS gene coding for the sigma38 factor;
k) the aspA gene coding for aspartate ammonium lyase; and
l) the aceB gene coding for malate synthase A.

In another aspect, the invention includes a microorganism from the Entero-bacteriaceae family, in which the activity of the product of the yfiD ORF and/or the pflB gene is enhanced, e.g., due to overexpression of the yfiD ORF or the pflB gene or due to the expression of other nucleotide sequences coding for the same products. Preferably, the microorganism is from the genus *Escherichia* and produces L-threonine.

DEFINITIONS

Figure 1:
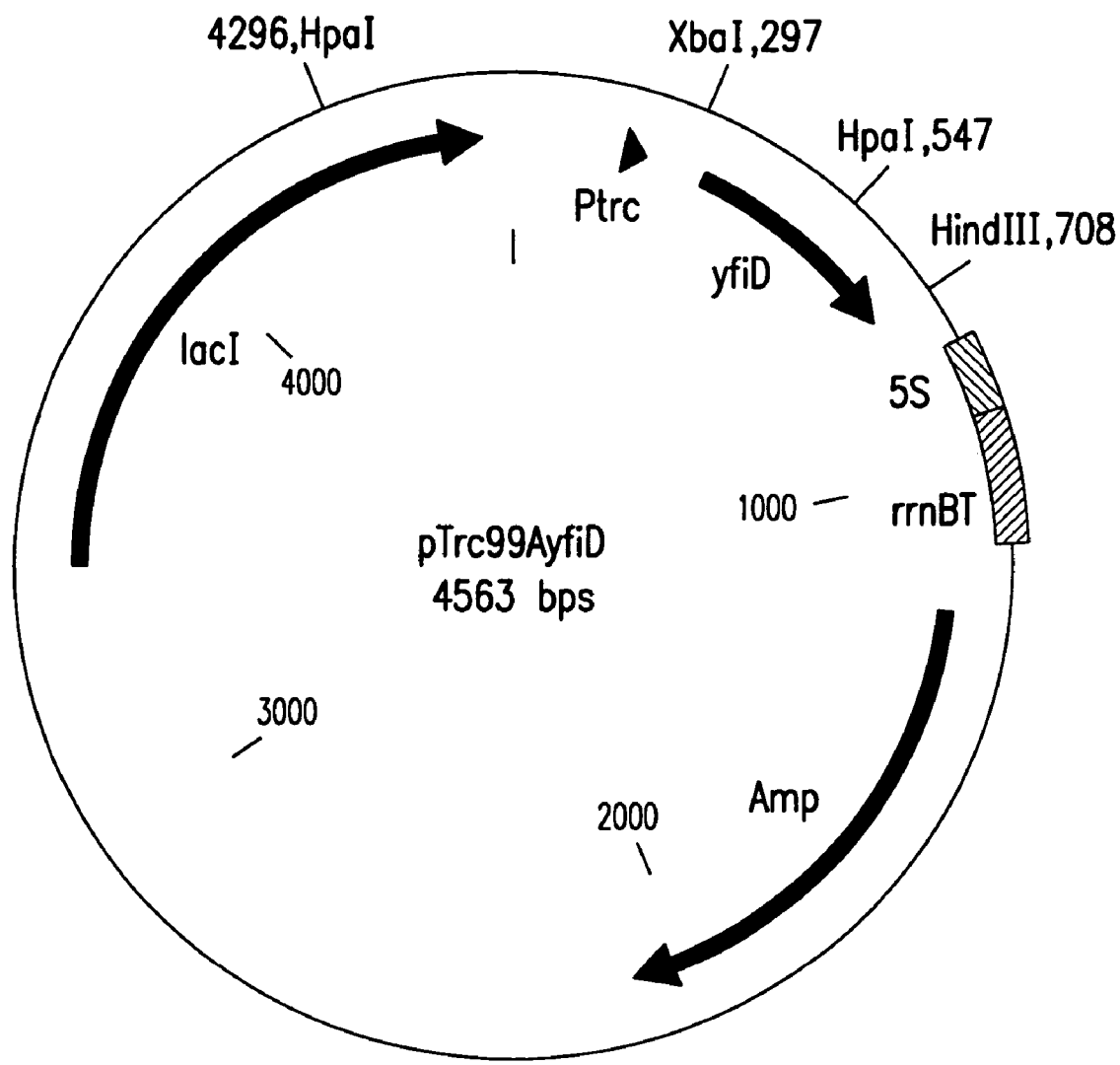
FIG. 1: Map of the vector pTrc99AyfiD.

When L-amino acids or amino acids are mentioned herein, it will be understood that this means one or more amino acids, including their salts, selected from the group comprising L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-threonine is particularly preferred.

The term "enhancement" in this context describes the increase in the intracellular activity or concentration of one or more enzymes or proteins in a microorganism which are encoded by the corresponding DNA. Enhancement may result from, for example: the number of copies of a gene or ORF being increased by at least one (1) copy; the use of a strong promoter; the use of a gene or allele that codes for a corresponding enzyme or protein with a high activity; and, optionally, by combining these measures.

The expression "open reading frame" (ORF) designates a segment of a nucleotide sequence that codes for, or can code for, a protein or, to be more exact, a polypeptide or ribonucleic acid, to which, according to the state of the art, no function can be assigned. After assignment of a function to the segment of the nucleotide sequence in question, one generally speaks of a gene.

The term "alleles" is generally understood to mean alternative forms of a given gene. The forms are distinguished by differences in the nucleotide sequence.

The expression "gene product" designates, in general, the protein encoded by a nucleotide sequence, i.e. an ORF, a gene or an allele, or the encoded ribonucleic acid.

By the measures of enhancement, in particular overexpression, the activity or concentration of the corresponding protein is generally increased by at least 10%, 25%, 50%, 75%, 100%, 150%, 200%, 300%, 400% or 500%, up to a maximum of 1000% or 2000%, relative to that of the wild-type protein or, to be more exact, the activity or concentration of the protein in the initial microorganism.

The expression "initial microorganism" or "parent strain" is understood to mean the microorganism in respect of which the measures according to the invention are carried out.

DETAILED DESCRIPTION OF THE INVENTION

The present invention provides a process for the production of L-amino acids by fermentation of recombinant microorganisms of the Enterobacteriaceae family, characterized in that:
 a) the microorganisms producing the desired L-aminoacid, in which the yfiD ORF and/or the pflB gene or nucleotide sequences or alleles coding for the gene products are enhanced, in particular overexpressed, are cultured in a medium under conditions in which the desired L-amino acid in the medium or in the cells is enriched, and
 b) the desired L-amino acid is isolated, whereby optionally constituents of the fermentation broth and/or the biomass in its entirety or in portions (>0 to 100%) remain in the isolated product or are completely removed.

The microorganisms, in particular recombinant microorganisms, which are provided by the present invention, are able to produce L-amino acids from glucose, sucrose, lactose, fructose, maltose, molasses, in appropriate circumstances starch, in appropriate circumstances cellulose, or from glycerin and ethanol. Such microorganisms are representatives of the Enterobacteriaceae family, preferably selected from the genera *Escherichia, Erwinia, Providencia* and *Serratia*. The genera *Escherichia* and *Serratia* are especially preferred. In the case of the genus *Escherichia*, the most preferred species is *Escherichia coli*, and in the case of the genus *Serratia*, the most preferred species is *Serratia marcescens*.

In general, recombinant microorganisms are generated by transformation, transduction or conjugation with a vector carrying the desired gene. Suitable strains of the genus *Escherichia*, in particular of the species *Escherichia coli*, which in particular, produce L-threonine, are, for example:

*Escherichia coli* H4581, (EP 0 301 572);
*Escherichia coli* KY10935, (*Biosci. Biotechnol. Biochem.* 61(11):1877–1882 (1997));
*Escherichia coli* VNIIgenetika MG442, (U.S. Pat. No. 4,278,765);
*Escherichia coli* VNIIgenetika M1, (U.S. Pat. No. 4,321,325);
*Escherichia coli* VNIIgenetika 472T23, (U.S. Pat. No. 5,631,157);
*Escherichia coli* BKIIM B-3996, (U.S. Pat. No. 5,175,107);
*Escherichia coli* kat 13, (WO 98/04715); and
*Escherichia coli* KCCM-10132 (WO 00/09660).

Suitable L-threonine-producing strains of the genus *Serratia*, in particular of the species *Serratia marcescens*, are, for example:

*Serratia marcescens* HNr21, (*Appl. and Envir. Microbiol.* 38(6):1045–1051 (1979));
*Serratia marcescens* TLr156 (*Gene* 57(2–3):151–158 (1987)); and
*Serratia marcescens* T-2000, (*Appl. Biochem. Biotechnol.* 37(3):255–265 (1992)).

L-threonine-producing strains from the Enterobacteriaceae family preferably possess, inter alia, one or more of the genetic or phenotypic features selected from the group comprising: resistance to α-amino-β-hydroxyvaleric acid, resistance to thialysine, resistance to ethionine, resistance to α-methylserine, resistance to diaminosuccinic acid, resistance to α-aminobutyric acid, resistance to borrelidin, resistance to cyclopentanecarboxylic acid, resistance to rifampicin, resistance to valine analogues such as, for example, valine hydroxamate, resistance to purine analogues such as, for example, 6-dimethylaminopurine, need for L-methionine, in appropriate circumstances partial and compensable need for L-isoleucine, need for meso-diaminopimelic acid, auxotrophy with respect to threonine-containing dipeptides, resistance to L-threonine, resistance to threonine raffinate, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, in appropriate circumstances the ability to utilize sucrose, enhancement of the threonine operon, enhancement of homoserine dehydrogenase I-aspartate kinase I, preferably of the feedback-resistant form, enhancement of homoserine kinase, enhancement of threonine synthase, enhancement of aspartate kinase, optionally of the feedback-resistant form, enhancement of aspartate semialdehyde dehydrogenase, enhancement of phosphoenolpyruvate carboxylase, optionally of the feedback-resistant form, enhancement of phosphoenolpyruvate synthase, enhancement of transhydrogenase, enhancement of the RhtB gene product, enhancement of the RhtC gene product, enhancement of the YfiK gene product, enhancement of a pyruvate carboxylase, and attenuation of the formation of acetic acid.

After enhancement, in particular overexpression, of the open reading frame yfiD and/or of the pflB gene or nucleotide sequence(s) or alleles coding for the corresponding gene products, microorganisms of the Enterobacteriaceae family produce L-amino acids, in particular L-threonine, in an improved manner. The nucleotide sequences of the genes or open reading frames (ORFs) of *Escherichia coli* can be found in the genome sequence of *Escherichia coli* published by Blattner et al. (*Science* 277:1453–1462 (1997)). The open reading frame yfiD and the protein coded by this ORF are described, inter alia, by the following data:

Designation: open reading frame;
Function: putative formate acetyl transferase;
Description: the open reading frame yfiD codes for a 14.3 kDa protein, the isoelectric point is situated at 5.1; localized chromosomally, it is situated, for example in the case of *Escherichia coli* K12 MG1655, in the intergenic region of the open reading frame yfiK, coding for a putative L-aspartate oxidase, and the ung gene, coding for uracil DNA glycosylase
Reference: Blankenhorn et al.; *J. Bacteriol.* 181(7):2209–2216 (1999);
Fountoulakis et al.; *Electrophoresis* 20(11): 2181–2195 (1999);
Kirkpatrick et al.; *J. Bacteriol.* 183(21):6466–6477 (2001);
Wybom et al.; *Microbiol.* 148:1015–1026 (2002).
Accession No.: AE000344

The pflB gene and the protein coded by this gene are described, inter alia, by the following data:

Designation: formate acetyl transferase I, pyruvate formate lyase I
EC No.: 2.3.1.54
Reference: Rodel et al.; *Eur. J. Biochem.* 177(1):153–158 (1988);
Wagner et al.; *Proc. Nat'l Acad. Sci. USA* 89(3): 996–1000 (1992).
Accession No.: AE000192
Alternative gene name: pfl The pyruvate formate lyase from Salmonella typhimurium is described, inter alia, in Wong et al., *J. Bacteriol.* 171(9):4900–4905 (1989).

The nucleic-acid sequences can be obtained from the databases of the National Center for Biotechnology Information (NCBI) of the National Library of Medicine (Bethesda, Md., USA), from the Nucleotide Sequence Database of the European Molecular Biology Laboratory (EMBL, Heidelberg, Germany, and Cambridge, UK) or from the DNA Data Bank of Japan (DDBJ, Mishima, Japan). For the sake of better clarity, the known sequence relating to the yfiD ORF is represented herein as SEQ ID NO:3. The protein coded by this reading frame is represented herein as SEQ ID NO:4.

The sequence specified in the sequence listing can be used in accordance with the invention. Use may also be made of alleles of the genes or open reading frames that result from the degeneracy of the genetic code or by virtue of functionally neutral sense mutations. The use of endogenous genes or of endogenous open reading frames is preferred. The expression "endogenous genes" or "endogenous nucleotide sequences" is understood to mean the genes or open reading frames or alleles or, to be more exact, nucleotide sequences, that are present in the population of a species.

The alleles that contain functionally neutral sense mutations include, inter alia, those which result in at least one (1) conservative amino-acid exchange in the protein coded by them. In the case of the aromatic amino acids, conservative exchanges occur when phenylalanine, tryptophan and tyrosine are exchanged for one another. In the case of the hydrophobic amino acids, conservative exchanges occur if leucine, isoleucine and valine are exchanged for one another. In the case of the polar amino acids, conservative exchanges occur if glutamine and asparagine are exchanged for one another. In the case of the basic amino acids, conservative exchanges occur if arginine, lysine and histidine are exchanged for one another. In the case of the acidic amino acids, conservative exchanges occur if aspartic acid and glutamic acid are exchanged for one another. In the case of the amino acids containing hydroxyl groups, conservative exchanges occur if serine and threonine are exchanged for one another.

Similarly, nucleotide sequences can be used which code for variants of the stated proteins which additionally contain at the N-terminus or C-terminus a lengthening or shortening of at least one (1) amino acid. This lengthening or shortening amounts to not more than 50, 40, 30, 20, 10, 5, 3 or 2 amino acids or amino-acid residues.

Suitable alleles also include those which code for proteins in which at least one (1) amino acid is inserted or deleted. The maximum number of such changes, which are designated as indels, may concern 2, 3, 5, 10, 20 but in no case more than 30 amino acids. The suitable alleles include, furthermore, those which can be obtained by hybridization, in particular under stringent conditions using SEQ ID NO:3 or SEQ ID NO:7 or parts thereof, particularly the coding regions or the sequences complementary thereto. Instructions on the identification of DNA sequences by means of hybridization can be found by a person skilled in the art, inter alia, in the manual entitled "The DIG System Users Guide for Filter Hybridization" produced by Boehringer Mannheim GmbH (Mannheim, Germany, 1993) and in Liebl et al. (*Internat'l J. Systematic Bacteriol.* 41:255–260 (1991)). The hybridization takes place under stringent conditions—i.e., only hybrids are formed in which the probe and the target sequence, i.e. the polynucleotides treated with the probe, are at least 70% identical. It is known that the stringency of the hybridization, including the washing steps, is influenced or determined by varying the composition of the buffer, the temperature, and the salt concentration. The hybridization reaction is generally carried out with relatively low stringency in comparison with the washing steps (*Hybaid Hybridisation Guide*, Hybaid Limited, Teddington, UK, 1996).

For the hybridization reaction, a buffer corresponding to 5×SSC buffer at a temperature of about 50° C.–68° C. can be employed. Under these conditions, probes can hybridize with polynucleotides that exhibit less than 70% identity to the sequence of the probe. Such hybrids are less stable and are removed by washing under stringent conditions. This can be attained, for example, by lowering the salt concentration to 2×SSC and optionally subsequently to 0.5×SSC (*The DIG System User's Guide for Filter Hybridisation*, Boehringer Mannheim, Mannheim, Germany, 1995), at a temperature of about 50° C.–68° C., about 52° C.–68° C., about 54° C.–68° C., about 56° C.–68° C., about 58° C.–68° C., about 60° C.–68° C., about 62° C.–68° C., about 64° C.–68° C. or about 66° C.–68° C. Optionally, he salt concentration may be lowered to a concentration corresponding to 0.2×SSC or 0.1×SSC. By stepwise increase of the hybridization temperature in steps of about 1–2° C. from 50° C. to 68° C., polynucleotide fragments can be isolated which, for example, possess at least 70% or at least 80% or at least 90% to 95% or at least 96% to 99% identity to the sequence of the probe employed. Further instructions on hybridization are commercially obtainable in the form of so-called kits (e.g., DIG Easy Hyb produced by Roche Diagnostics GmbH, Mannheim, Germany, Catalogue No. 1603558).

To enhance activity, the expression of the genes or open reading frames or alleles can be increased, or the catalytic or regulatory properties (activity) of the proteins can be enhanced. Both measures may optionally be combined.

Overexpression may be accomplished by increasing the number of copies of the corresponding genes or open reading frames, or by mutating the promoter and regulation region or the ribosome binding site, which is located upstream of the structural gene. Expression cassettes which are incorporated upstream of the structural gene act in like manner. Expression can also be increased using inducible promoters or by prolonging the lifespan of mRNA. By preventing the degradation of the enzyme protein, enzyme activity is likewise enhanced. The genes or gene constructs may either be present in extra-chromosomally replicating plasmids with a different number of copies or may be integrated within the chromosome and amplified.

Alternatively overexpression can be obtained by changing the composition of the media and by culture management. Instructions on this can be found, inter alia, in Chang, et al. (*J. Bacteriol.* 134:1141–1156 (1978)), in Hartley, et al. (*Gene* 13:347–353 (1981)), in Amann, et al. (*Gene* 40:183–190 (1985)), in de Broer, et al. (*Proc. Nat'l Acad. Sci. USA* 80: 21–25 (1983)), in LaVallie et al. (*BIO/TECHNOLOGY* 11:187–193 (1993)), in WO98/04715, in Llosa, et al. (*Plasmid* 26:222–224 (1991)), in Quandt, et al., (*Gene* 80: 61–169 (1989)), in Hamilton, et al. (*J. Bacteriol.* 171: 4617–4622 (1989)), in Jensen, et al., (*Biotech. Bioeng.* 58:191–195 (1998)) and in textbooks on genetics and molecular biology.

Use may be made of plasmid vectors capable of replicating in Enterobacteriaceae, such as cloning vectors derived from pACYC184 (Bartolomé, et al., *Gene* 102:75–78 (1991)), pTrc99A (Amann et al.; *Gene* 69:301–315 (1988)) or pSC101 derivatives (Vocke, et al., *Proc. Nat'l Acad. Sci. USA* 80(21):6557–6561 (1983)). A strain transformed with a plasmid vector can be employed in a process according to the invention, in which case the plasmid vector carries at least the yfiD ORF and/or the pflB gene or nucleotide sequences or alleles coding for the gene products thereof.

The term "transformation refers to the uptake of a nucleic acid by a host (microorganism). It is likewise possible to transfer mutations that relate to the expression of the respective genes or open reading frames into various strains by sequence exchange (Hamilton et al., *J. Bacteriol.* 171: 4617–4622 (1989)), conjugation or transduction. Detailed explanations relating to the terms of genetics and molecular biology can be found in textbooks on genetics and molecular biology, such as the textbook by Birge (*Bacterial and Bacteriophage Genetics*, 4$^{th}$ ed., Springer Verlag, New York (USA), 2000), the textbook by Berg, et al. (*Biochemistry*, 5$^{th}$ ed., Freeman and Company, New York (USA), 2002), or the textbook by Sambrook, et al. (*Molecular Cloning, A Laboratory Manual*, (3-volume set), Cold Spring Harbor Laboratory Press, Cold Spring Harbor (USA), 2001).

The production of L-amino acids may also be improved by enhancing one or more enzymes of the known threonine-biosynthesis pathway, enzymes of anaplerotic metabolism, enzymes for the production of reduced nicotinamide adenine dinucleotide phosphate, enzymes of glycolysis, PTS enzymes, or enzymes of sulfur metabolism. The use of endogenous genes is generally preferred. Examples of genes that may be enhanced, preferably by being overexpressed, include:

the thrABC operon coding for aspartate kinase, homoserine dehydrogenase, homoserine kinase and threonine synthase (U.S. Pat. No. 4,278,765);

the pyc gene of Corynebacterium glutamicum coding for pyruvate carboxylase (WO 99/18228);

the pps gene coding for phosphoenolpyruvate synthase (*Mol. Gen. Genet.* 231(2):332–336 (1992));

the ppc gene coding for phosphoenolpyruvate carboxylase (*Gene* 31:279–283 (1984));

the genes pntA and pntB coding for transhydrogenase (*Eur. J. Biochem.* 158:647–653 (1986));

the gene rhtB imparting homoserine resistance (EP-A-0 994 190);

the mqo gene coding for malate:quinine oxidoreductase (WO 02/06459);

the rhtC gene imparting threonine resistance (EP-A-1 013 765);

thrE gene of Corynebacterium glutamicum coding for the threonine-export protein (WO 01/92545);

the gdhA gene coding for glutamate dehydrogenase (*Nucl. Ac. Res.* 11:5257–5266 (1983); *Gene* 23:199–209 (1983));

the hns gene coding for the DNA binding protein HLP-II (WO 03/004671);

the pgm gene coding for phosphoglucomutase (WO 03/004598);

the fba gene coding for fructose biphosphate aldolase (WO 03/004664);

the ptsH gene of the ptsHIcrr operon coding for the phosphohistidine protein hexose phosphotransferase of the phosphotransferase system PTS (WO 03/004674);

the ptsI gene of the ptsHIcrr operon coding for enzyme I of the phosphotransferase system PTS (WO 03/004674);

the crr gene of the ptsHIcrr operon coding for the glucose-specific IIA component of the phosphotransferase system PTS (WO 03/004674);

the ptsG gene coding for the glucose-specific IIBC component (WO 03/004670);

the lrp gene coding for the regulator of the leucine regulon (WO 03/004665);

the csrA gene coding for the global regulator Csr (*J. Bacteriol.* 175:4744–4755 (1993));

the fadR gene coding for the regulator of the fad regulon (*Nucl. Ac. Res.* 16:7995–8009 (1988));

the iclR gene coding for the regulator of central intermediary metabolism (*J. Bacteriol.* 172: 2642–2649 (1990));

the mopB gene coding for the 10 kDa chaperon (WO 03/004669), which is also known under the designation "groES;"

the ahpC gene of the ahpCF operon coding for the small subunit of alkyl hydroperoxide reductase (WO 03/004663);

the ahpF gene of the ahpCF operon coding for the large subunit of alkyl hydroperoxide reductase (WO 03/004663);

the cysK gene coding for cysteine synthase A (WO 03/006666);

the cysB gene coding for the regulator of the cys regulon (WO 03/006666);

the cysJ gene of the cysJIH operon coding for the flavoprotein of NADPH sulfite reductase (WO 03/006666);

the cysI gene of the cysJIH operon coding for the haemoprotein of NADPH sulfite reductase (WO 03/006666);

the cysH gene of the cysJIH operon coding for adenylyl sulfate reductase (WO 03/006666);

the phoB gene of the phoBR operon coding for the positive regulator PhoB of the pho regulon (WO 03/008606);

the phoR gene of the phoBR operon coding for the sensor protein of the pho regulon (WO 03/008606);

the phoE gene coding for protein E of the outer cell membrane (WO 03/008608);

the pykF gene coding for pyruvate kinase I which is stimulated by fructose (WO 03/008609);

the pfkB gene coding for 6-phosphofructokinase II (WO 03/008610);

the malE gene coding for the periplasmic binding protein of maltose transport (WO 03/008605);

the sodA gene coding for superoxide dismutase (WO 03/008613);

the rseA gene of the rseABC operon coding for a membrane protein with anti-sigmaE activity (WO 03/008612);

the rseC gene of the rseABC operon coding for a global regulator of the sigmaE factors (WO 03/008612);

the sucA gene of the sucABCD operon coding for the decarboxylase subunit of 2-ketoglutarate dehydrogenase (WO 03/008614);

the sucB gene of the sucABCD operon coding for the dihydrolipoyl transsuccinase E2 subunit of 2-ketoglutarate dehydrogenase (WO 03/008614);

the sucC gene of the suc ABCD operon coding for the β-subunit of succinyl-CoA synthetase (WO 03/008615);

the sucD gene of the sucABCD operon coding for the α-subunit of succinyl-CoA synthetase (WO 03/008615);

the adk gene coding for adenylate kinase (*Nucl. Ac. Res.* 13(19):7139–7151 (1985));

the hdeA gene coding for a periplasmic protein with chaperonin-type function (*J. Bacteriol.* 175(23):7747–7748 (1993));

the hdeB gene coding for a periplasmic protein with chaperonin-type function (*J. Bacteriol.* 175(23):7747–7748 (1993));

the icd gene coding for isocitrate dehydrogenase (*J. Biol. Chem.* 262(22):10422–10425 (1987));

the mglB gene coding for the periplasmic, galactose-binding transport protein (*Mol. Gen. Genet.* 229(3):453–459 (1991));

the lpd gene coding for dihydrolipoamide dehydrogenase (*Eur. J. Biochem.* 135(3):519–527 (1983));

the aceE gene coding for the E1 component of the pyruvate-dehydrogenase complex (*Eur. J. Biochem.* 133(1):155–162 (1983));

the aceF gene coding for the E2 component of the pyruvate-dehydrogenase complex (*Eur. J. Biochem.* 133(3):481–489 (1983));

the pepB gene coding for aminopeptidase B (*J. Fermentation Bioeng.* 82:392–397 (1996));

the aldH gene coding for aldehyde dehydrogenase (E.C. 1.2.1.3) (*Gene* 99(1):15–23 (1991));

the bfr gene coding for the iron-storage homoprotein (bacterioferritin) (*J. Bacteriol.* 171(7):3940–3947 (1989));

the udp gene coding for uridine phosphorylase (*Nucl. Ac. Res.* 17(16): 6741 (1989)) and the rseB gene coding for the regulator of sigmaE-factor activity (*Mol. Microbiol.* 24(2): 355–371 (1997)).

It may also be advantageous, in addition to the enhancement of the yfiD ORF and/or of the pflB gene, to attenuate (in particular to eliminate or to diminish the expression of) one or more of the following:

the tdh gene coding for threonine dehydrogenase (*J. Bacteriol.* 169:4716–4721 (1987));

the mdh gene coding for malate dehydrogenase (E.C. 1.1.1.37) (*Arch. Microbiol.* 149:36–42 (1987));

the gene product of the open reading frame (ORF) yjfA (Accession Number AAC77180 of the National Center for Biotechnology Information (NCBI, Bethesda, Md., USA) WO 02/29080);

the gene product of the open reading frame (ORF) ytfp (Accession Number AAC77179 of the National Center for Biotechnology Information (NCBI, Bethesda, Md., USA)), WO 02/29080);

the pckA gene coding for the enzyme phosphoenolpyruvate carboxykinase (WO 02/29080);

the poxB gene coding for pyruvate oxidase (WO 02/36797);

the aceA gene coding for the enzyme isocitrate lyase (WO 02/081722);

the dgsA gene coding for the DgsA regulator of the phosphotransferase system (WO 02/081721), which is also known under the designation "mlc gene;"

the fruR gene coding for the fructose repressor (WO 02/081698), which is also known as the "cra gene;"

the rpoS gene coding for the sigma$^{38}$ factor (WO 01/05939), which is also known as the "katF gene;"

the aspA gene coding for aspartate ammonium lyase (WO 03/008603); and the aceB gene coding for malate synthase A (WO 03/008604).

The term "attenuation" in this context describes the diminution or elimination of the intracellular activity or concentration of one or more enzymes or proteins in a microorganism that is/are encoded by the corresponding DNA. This may be accomplished, for example, through the use of a weak promoter or a gene or allele that codes for a corresponding enzyme or protein with a low activity or that inactivates the corresponding enzyme or protein or the open reading frame or the gene, and by optionally combining these measures. By the measures of attenuation, the activity or concentration of the corresponding protein is generally lowered to 0 to 75%, 0 to 50%, 0 to 25%, 0 to 10% or 0 to 5% of the activity or concentration of the wild-type protein or, to be more exact, of the activity or concentration of the protein in the initial microorganism.

The production of L-amino acids in microorganisms with enhanced activity of the yfiD ORF product and/or the pflB gene product, may also benefit from the elimination of one or more side reactions (Nakayama: "Breeding of Amino Acid Producing Microorganisms," in: *Overproduction of Microbial Products*, Krumphanzl, Sikyta, Vanek (eds.), Academic Press, London, UK, 1982). The microorganisms produced in accordance with the invention can be cultured in the batch process, in the fed-batch process or in the repeated fed-batch process. A summary of known cultivation methods is described in the textbook by Chmiel (*Bioprozesstechnik* 1. *Einführung in die Bioverfahrenstechnik* (Gustav Fischer Verlag, Stuttgart, 1991)) and in the textbook by Storhas (*Bioreaktoren and periphere Einrichtungen* (Vieweg Verlag, Braunschweig/Wiesbaden, 1994)).

The culture medium that is to be used has to satisfy the demands of the respective strains in a suitable manner. Descriptions of culture media of various microorganisms are contained in the manual entitled *Manual of Methods for General Bacteriology* produced by The American Society for Bacteriology (Washington D.C., USA, 1981). For a carbon source, use may be made of sugar and carbohydrates such as glucose, sucrose, lactose, fructose, maltose, molasses, starch and, in appropriate circumstances, cellulose, oils and fats such as, for example, soybean oil, sunflower oil, peanut oil and copra oil, fatty acids such as, for example, palmitic acid, stearic acid and linoleic acid, alcohols such as, for example, glycerin and ethanol, and organic acids such as, for example, acetic acid. These substances may be used individually or in the form of a mixture.

For a nitrogen source, use may be made of organic nitrogenous compounds such as peptones, yeast extract, meat extract, malt extract, corn steep liquor, soybean flour and urea or inorganic compounds such as ammonium sulfate, ammonium chloride, ammonium phosphate, ammonium carbonate and ammonium nitrate. The nitrogen sources may be used individually or in the form of a mixture.

For a phosphorus source, use may be made of phosphoric acid, potassium dihydrogenphosphate or dipotassium hydrogenphosphate or the corresponding sodium-containing salts. The culture medium must also contain salts of metals, such as magnesium sulfate or iron sulfate, that are necessary for growth. Finally, essential growth-regulating substances such as amino acids and vitamins may be employed in addition to the aforementioned substances. Suitable precursors may, moreover, be added to the culture medium. The stated feed materials may be added to the culture in the form of a single batch or may be fed in during the cultivation in suitable manner.

The fermentation is generally carried out at a pH value from 5.5 to 9.0, in particular 6.0 to 8.0. For the purpose of controlling the pH of the culture, basic compounds such as sodium hydroxide, potassium hydroxide, ammonia or ammoniacal liquor or acidic compounds such as phosphoric acid or sulfuric acid are employed in suitable manner. For the purpose of controlling the evolution of foam, anti-foaming agents such as, for example, fatty-acid polyglycol esters may be employed. For the purpose of maintaining the stability of plasmids, suitable substances acting selectively, for example antibiotics, may be added to the medium. In order to maintain aerobic conditions, oxygen or oxygen-containing gas mixtures, such as air for example, are introduced into the culture. The temperature of the culture is normally around 25° C. to 45° C. and preferably around 30° C. to 40° C.

The culture is carried on until such time as a maximum of L-amino acids, preferably L-threonine, has formed. This objective is normally attained within 10 hours to 160 hours. The analysis of L-amino acids can be undertaken by anion-exchange chromatography with subsequent ninhydrin derivation, as described in Spackman, et al. (*Anal. Chem.* 30:1190–1206 (1958)), or it can be undertaken by reversed phase HPLC, as described in Lindroth, et al. (*Anal. Chem.* 51:1167–1174 (1979)).

The process according to the invention may be used for the fermentative production of L-amino acids, such as, for example, L-threonine, L-isoleucine, L-valine, L-methionine, L-homoserine and L-lysine, in particular L-threonine.

The present invention may be further understood based upon the following non-limiting examples.

EXAMPLES

Minimal media (M9) and complete media (LB) that are used for *Escherichia coli* are described by J. H. Miller (A short course in bacterial genetics (1992), Cold Spring Harbor Laboratory Press). The isolation of plasmid DNA from *Escherichia coli* and also all techniques relating to restriction, ligation, Klenow treatment and alkaline phosphatase treatment are carried out in accordance with Sambrook et al. (*Molecular Cloning—A Laboratory Manual* (1989) Cold Spring Harbor Laboratory Press). The transformation of *Escherichia coli* is carried out, unless described otherwise, in accordance with Chung, et al. (*Proc. Nat'l Acad. Sci. USA* 86:2172–2175 (1989)). The incubation temperature in the course of the production of strains and transformants is 37° C.

Example 1

1.1 Construction of the Expression Plasmid pTrc99AyfiD

The open reading frame yfiD from *E. coli* K12 is amplified by using the polymerase chain reaction (PCR) and also synthetic oligonucleotides. Starting from the nucleotide sequence of the open reading frame yfiD in *E. coli* K12 MG1655 (Accession Number AE000344, Blattner et al. (*Science* 277:1453–1474 (1997)), PCR primers are synthesized (MWG Biotech, Ebersberg, Germany). The primers contain sequences for restriction enzymes, which are marked by underlining in the nucleotide sequence represented below. The primer yfiD1 contains the restriction site for XbaI; the primer yfiD2 contains the restriction site for HindIII.

yfiD1:

5' - GAACAAA<u>TCTAGA</u>AAATTAAGCCGGGGAGGC   (SEQ ID NO:1) -3' yfiD2:

5' - GCTACTT<u>AAGCTT</u>TACAGGCTTTC - 3'   (SEQ ID NO:2)

The chromosomal *E. coli* K12 MG1655 DNA employed for the PCR is isolated in accordance with the manufacturer's directions using "Qiagen Genomic-tips 100/G" (QIAGEN, Hilden, Germany). A DNA fragment with a size of about 431 bp can be amplified with the specific primers under standard PCR conditions (Innis et al. (1990) PCR Protocols. A guide to methods and applications, Academic Press) with Vent-DNA-Polymerase (New England Biolabs, Frankfurt, Germany) (SEQ ID NO:3).

The PCR product is restricted with the restriction enzymes HindIII and XbaI and examined in a 0.8% agarose gel after being cleaned up (Purification Kit, QIAGEN, Hilden, Germany). The vector pTrc99A (Pharmacia Biotech, Uppsala, Sweden) is cleaved with the enzymes HindIII and XbaI, and ligated with the restricted yfiD fragment. The *E. coli* strain XL1-Blue MRF' (Stratagene, La Jolla, USA) is transformed with the ligation batch, and plasmid-bearing cells are selected on LB agar to which 50 µg/ml ampicillin have been added. The successful cloning can be demonstrated after the isolation of plasmid DNA by control cleavage with the enzymes HindIII/XbaI and HpaI. The plasmid is designated as pTrc99AyfiD (FIG. 1).

1.2 Construction of the Expression Plasmid pTrc99ApflB

The pflB gene from *E. coli* K12 is amplified by using the polymerase chain reaction (PCR) and also synthetic oligonucleotides. Starting from the nucleotide sequence of the pflB gene in *E. coli* K12 MG1655 (Accession Number AE000192, Blattner et al. (*Science* 277:1453–1474 (1997)), PCR primers are synthesized (MWG Biotech, Ebersberg, Germany). The primers contain sequences for restriction enzymes, which are marked by underlining in the nucleotide sequence represented below. The primer pflB1 contains the restriction site for XbaI; the primer pflB2 contains the restriction site for HindIII.

pflB1:

5' - CCAC<u>TCTAGA</u>AGGTAGGTGTTACATGTC -3'   (SEQ ID NO:5)

pflB2:

5' - CGATTTCAGTC<u>AAAGCTT</u>ATTACATAG -   (SEQ ID NO:6) 3'.

The chromosomal *E. coli* K12 MG1655 DNA employed for the PCR is isolated in accordance with the manufacturer's directions using "Qiagen Genomic-tips 100/G" (QIAGEN, Hilden, Germany). A DNA fragment with a size of about 2325 bp can be amplified with the specific primers under standard PCR conditions (Innis et al. (1990) PCR Protocols. A guide to methods and applications, Academic Press) with Vent-DNA-Polymerase (New England Biolabs, Frankfurt, Germany) (SEQ ID No. 7).

Figure 2:
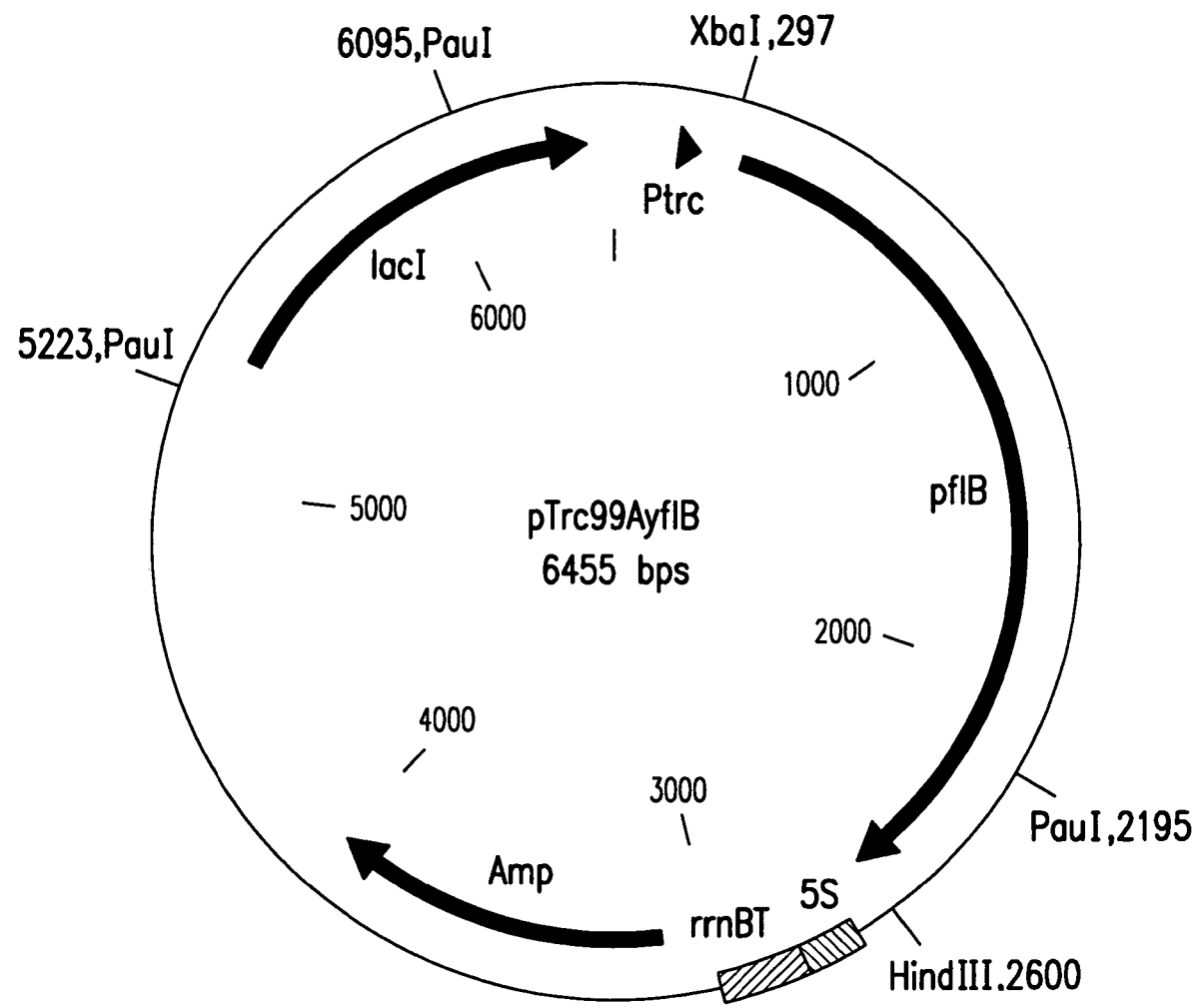
FIG. 2: Map of the vector pTrc99ApflB.
In both FIG. 1 and FIG. 2, length data are to be interpreted as approximate. The abbreviations and designations that are used have the following significance:
Amp: ampicillin-resistance gene;
lacI: gene for the repressor protein of the trc promoter;
Ptrc: trc promoter region, IPTG-inducible;
yfiD: coding region of the open reading frame yfiD;
pflB: coding region of the pflB gene;
5S: 5S rRNA region;
rrnBT: rRNA terminator region.
The abbreviations for the restriction enzymes have the following significance:
HindIII: restriction endonuclease from *Haemophilus influenze* $R_C$;
HpaI: restriction endonuclease from *Haemophilus parainfluenzae;*
PauI: restriction endonuclease from *Paracoccus alcaliphilus;*
XbaI: restriction endonuclease from *Xanthomonas campestris.*

The PCR product is restricted with the restriction enzymes HindIII and XbaI and examined in a 0.8% agarose gel after being cleaned up (Purification Kit, QIAGEN, Hilden, Germany). The vector pTrc99A (Pharmacia Biotech, Uppsala, Sweden) is cleaved with the enzymes HindIII and XbaI, and ligated with the restricted pflB fragment. The *E. coli* strain XL1-Blue MRF' (Stratagene, La Jolla, USA) is transformed with the ligation batch, and plasmid-bearing cells are selected on LB agar to which 50 μg/ml ampicillin have been added. The successful cloning can be demonstrated after the isolation of plasmid DNA by control cleavage with the enzymes HindIII/XbaI and PauI. The plasmid is designated as pTrc99ApflB (FIG. 2).

Example 2

2.1 Production of L-Threonine with the Strain MG442/pTrc99AyfiD

The L-threonine-producing *E. coli* strain MG442 is described in patent specification U.S. Pat. No. 4,278,765 and deposited at the Russian National Collection of Industrial Microorganisms (VKPM, Moscow, Russia) as CMIM B-1628. The strain MG442 is transformed with the expression plasmid pTrc99AyfiD described in Example 1.1 and with the vector pTrc99A, and plasmid-bearing cells are selected on LB agar with 50 μg/ml ampicillin. In this way, the strains MG442/pTrc99AyfiD and MG442/pTrc99A arise. Selected single colonies are subsequently multiplied further on minimal medium having the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 2 g/l glucose, 20 g/l agar, 50 mg/l ampicillin. The formation of L-threonine is examined in batch cultures of 10 ml, which are contained in 100 ml Erlenmeyer flasks. To this end, 10 ml of preculture medium having the following composition: 2 g/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l glucose, 50 mg/l ampicillin, are inoculated and incubated for 16 hours at 37° C. and at 180 rpm in an ESR incubator manufactured by Kühner AG (Birsfelden, Switzerland). 250 μl at a time of this preculture are inoculated into 10 ml of production medium (25 g/l $(NH_4)_2SO_4$, 2 g/l $KH_2PO_4$, 1 g/l $MgSO_4*7H_2O$, 0.03 g/l $FeSO_4*7H_2O$, 0.018 g/l $MnSO_4*1H_2O$, 30 g/l $CaCO_3$, 20 g/l glucose, 50 mg/l ampicillin) and incubated for 48 hours at 37° C. The formation of L-threonine by the initial strain MG442 is examined in the same way, there being, however, no addition of ampicillin to the medium. After the incubation, the optical density (OD) of the culture suspension is determined at a measuring wavelength of 660 nm with an LP2W photometer manufactured by Dr. Lange (Düsseldorf, Germany). Subsequently the concentration of L-threonine which has formed is determined in the sterile-filtered culture supernatant with an amino-acid analyzer manufactured by Eppendorf-BioTronik (Hamburg, Germany), by ion-exchange chromatography and post-column reaction with detection of ninhydrin. The result of the experiment is presented in Table 1.

TABLE 1

| Strain | OD (660 nm) | L-threonine g/l |
|---|---|---|
| MG442 | 5.6 | 1.4 |
| MG442/pTrc99A | 3.8 | 1.3 |
| MG442/pTrc99AyfiD | 5.5 | 2.5 |

2.2 Production of L-Threonine with the Strain MG442/pTrc99ApflB

The L-threonine-producing *E. coli* strain MG442 is described in patent specification U.S. Pat. No. 4,278,765 and deposited at the Russian National Collection of Industrial Microorganisms (VKPM, Moscow, Russia) as CMIM B-1628. The strain MG442 is transformed with the expression plasmid pTrc99ApflB described in Example 1.2 and with the vector pTrc99A, and plasmid-bearing cells are selected on LB agar with 50 μg/ml ampicillin. In this way, the strains MG442/pTrc99ApflB and MG442/pTrc99A arise. Selected single colonies are subsequently multiplied further on minimal medium having the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 2 g/l glucose, 20 g/l agar, 50 mg/l ampicillin. The formation of L-threonine is examined in batch cultures of 10 ml, which are contained in 100 ml Erlenmeyer flasks. To this end, 10 ml of preculture medium having the following composition: 2μg/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l glucose, 50 mg/l ampicillin, are inoculated and incubated for 16 hours at 37° C. and 180 rpm in an ESR incubator manufactured by Kühner AG (Birsfelden, Switzerland). 250 μl at a time of this preculture are inoculated into 10 ml of production medium (25 g/l $(NH_4)_2SO_4$, 2 g/l $KH_2PO_4$, 1 g/l $MgSO_4*7H_2O$, 0.03 g/l $FeSO_4*7H_2O$, 0.018 g/l $MnSO_4*1H_2O$, 30 g/l $CaCO_3$, 20 g/l glucose, 50 mg/l ampicillin) and incubated for 48 hours at 37° C. With a view to complete induction of the expression of the pflB gene, 100 mg/l isopropyl-β-D-thiogalactopyranoside (IPTG) are added in parallel batches. The formation of L-threonine by the initial strain MG442 is examined in the same way, there being, however, no addition of ampicillin to the medium. After the incubation, the optical density (OD) of the culture suspension is determined at a measuring wavelength of 660 nm with an LP2W photometer manufactured by Dr. Lange (Düsseldorf, Germany). Subsequently the concentration of L-threonine which has formed is determined in the sterile-filtered culture supernatant with an amino-acid analyzer manufactured by Eppendorf-BioTronik (Hamburg, Germany), by ion-exchange chromatography and post-column reaction with detection of ninhydrin. The result of the experiment is presented in Table 2.

TABLE 2

| Strain | Additives | OD (660 nm) | L-threonine g/l |
|---|---|---|---|
| MG442 | — | 5.6 | 1.4 |
| MG442/pTrc99A | — | 3.8 | 1.3 |
| MG442/pTrc99ApflB | — | 5.6 | 1.9 |
| MG442/pTrc99ApflB | IPTG | 5.2 | 2.2 |

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A process for the production of an L-amino acid comprising:
   a) culturing a recombinant microorganism from the Enterobacteriaceae family in a fermentation medium, wherein;
      i) said recombinant microorganism produces said L-amino acid;
      ii) said recombinant microorganism has been transformed with a vector comprising an open reading frame (ORF) that encodes a protein comprising the amino acid sequence of SEQ ID NO:4;
      iii) said ORF is overexpressed in said recombinant microorganism by increasing the copy number of said ORF or by linking said ORF to a promoter;
   b) allowing said fermentation medium or said recombinant microorganism to become enriched in said L-amino acid; and
   b) isolating said L-amino acid.

2. The process of claim 1, wherein said ORF encodes protein that consists of the amino acid sequence of SEQ ID NO:4.

3. The process of claim 1 wherein some or all of the constituents of said fermentation medium and/or the biomass of said recombinant microorganism are isolated with said L-amino acid.

4. The process of claim 1 wherein said ORF that encodes a protein with the amino acid sequence of SEQ ID NO:4 comprises the nucleotide sequence of SEQ ID NO:3.

5. The process of claim 4 wherein said ORF that encodes a protein with the amino acid sequence of SEQ ID NO:4 consists of the nucleotide sequence of SEQ ID NO:3.

6. The process of claim 1, wherein the genus of said recombinant microorganism is selected from the group consisting of: *Escherichia*; *Erwinia*; *Providencia*; and *Serratia*.

7. The process of claim 1, wherein said microorganism overexpresses said ORF and, in addition, the activity of one or more additional *E. coli* genes is overexpressed, said one or more additional genes being selected from the group consisting of:
   a) the *E. coli* thrABC operon coding for aspartate kinase, homoserine dehydrogenase, homoserine kinase and threonine synthase;
   b) the *C. glutamicum* pyc gene coding for pyruvate carboxylase;
   c) the *E. coli* pps gene for phosphoenolpyruvate synthase;
   d) the *E. coli* ppc gene coding for phosphoenolpyruvate carboxylase;
   e) the *E. coli* genes pntA and pntB coding for transhydrogenase;
   f) the *E. coli* rhtB gene imparting homoserine resistance;
   g) the *E. coli* mqo gene coding for malate:quinone oxidoreductase;
   h) the *E. coli* rhtC gene imparting threonine resistance;
   i) the *C. glutamicum* thrE gene coding for the threonine-export protein;

j) the *E. coli* gdhA gene coding for glutamate dehydrogenase;
k) the *E. coli* hns gene coding for the DNA binding protein HLP-II;
l) the *E. coli* pgm gene coding for phosphoglucomutase;
m) the *E. coli* fba gene coding for fructose biphosphate aldolase;
n) the *E. coli* ptsH gene coding for phosphohistidine protein hexose phosphotransferase;
o) the *E. coli* ptsI gene coding for enzyme I of the phosphotransferase system;
p) the *E. coli* crr gene coding for the glucose-specific IIA component;
q) the *E. coli* ptsG gene coding for the glucose-specific IIBC component;
r) the *E. coli* lrp gene coding for the regulator of the leucine regulon;
s) the *E. coli* csrA gene coding for the global regulator Csr;
t) the *E. coli* fadR gene coding for the regulator of the fad regulon;
u) the *E. coli* iclR gene coding for the regulator of central intermediary metabolism;
v) the *E. coli* mopB gene coding for the 10 kDa chaperon;
w) the *E. coli* ahpC gene coding for the small subunit of alkyl hydroperoxide reductase;
x) the *E. coli* ahpF gene coding for the large subunit of alkyl hydroperoxide reductase;
y) the *E. coli* cysK gene coding for cysteine synthase A;
z) the *E. coli* cysB gene coding for the regulator of the cys regulon;
aa) the *E. coli* cysJ gene coding for the flavoprotein of NADPH sulfite reductase;
bb) the *E. coli* cysI gene coding for the haemoprotein of NADPH sulfite reductase;
cc) the *E. coli* cysH gene coding for adenylyl sulfate reductase;
dd) the *E. coli* phoB gene coding for the positive regulator PhoB of the pho regulon;
ee) the *E. coli* phoR gene coding for the sensor protein of the pho regulon;
ff) the *E. coli* phoE gene coding for protein E of the outer cell membrane;
gg) the *E. coli* pykE gene coding for pyruvate kinase I, which is stimulated by fructose;
hh) the *E. coli* pfkB gene coding for 6-phosphofructokinase II;
ii) the *E. coli* malE gene coding for the periplasmic binding protein of maltose transport;
jj) the *E. coli* sodA gene coding for superoxide dismutase;
kk) the *E. coli* rseA gene coding for a membrane protein with anti-sigmaE activity;
ll) the *E. coli* rseC gene coding for a global regulator of the sigmaE factor;
mm) the *E. coli* sucA gene coding for the decarboxylase subunit of 2-ketoglutarate dehydrogenase;
nn) *E. coli* the sucB gene coding for the dihydrolipoyl transsuccinase E2 subunit of 2-ketoglutarate dehydrogenase;
oo) *E. coli* the sucC gene coding for the β-subunit of succinyl-CoA synthetase;
pp) the *E. coli* sucD gene coding for the α-subunit of succinyl-CoA synthetase;
qq) the *E. coli* adk gene coding for adenylate kinase;
rr) the *E. coli* hdeA gene coding for a periplasmic protein with chaperonin-type function;

ss) the *E. coli* hdeB gene coding for a periplasmic protein with chaperonin-type function;
tt) the *E. coli* icd gene coding for isocitrate dehydrogenase;
uu) the *E. coli* mglB gene coding for the periplasmic, galactose-binding transport protein;
vv) the *E. coli* lpd gene coding for dihydrolipoamide dehydrogenase;
ww) the *E. coli* aceE gene coding for the E1 component of the pyruvate-dehydrogenase complex;
xx) the *E. coli* aceF gene coding for the E2 component of the pyruvate-dehydrogenase complex;
yy) the *E. coli* pepB gene coding for aminopeptidase B;
zz) the *E. coli* aldH gene coding for aldehyde dehydrogenase,
aaa) the *E. coli* bfr gene coding for the iron-storage homoprotein;
bbb) the *E. coli* udp gene coding for uridine phosphorylase; and
ccc) the *E. coli* rseB gene coding for the regulator of sigmaE-factor activity.

8. The process of claim 1, wherein said L-amino acid is selected from the group consisting of: L-threonine; L-lysine; L-isoleucine, L-valine, L-methionine, and L-homoserine.

9. The process of claim 1, wherein said L-amino acid is either L-threonine or L-lysine.

10. The process of claim 8, wherein said ORF encodes protein that consists of the amino acid sequence of SEQ ID NO:4.

11. The process of claim 8, wherein some or all of the constituents of said fermentation medium and/or the biomass of said recombinant microorganism are isolated with said L-amino acid.

12. The process of claim 8, wherein said ORF that encodes a protein with the amino acid sequence of SEQ ID NO:4 comprises the nucleotide sequence of SEQ ID NO:3.

13. The process of claim 12 wherein said ORF that encodes a protein with the amino acid sequence of SEQ ID NO:4 consists of the nucleotide sequence of SEQ ID NO:3.

14. The process of claim 8, wherein the genus of said recombinant microorganism is selected from the group consisting of: *Escherichia*; *Erwinia*; *Providencia*; and *Serratia*.

15. The process of claim 8, wherein said microorganism overexpresses said ORF and, in addition, the activity of one or more additional *E. coli* genes is overexpressed, said one or more additional genes being selected from the group consisting of:
a) the *E. coli* thrABC operon coding for aspartate kinase, homoserine dehydrogenase, homoserine kinase and threonine synthase;
b) the *C. glutamicum* pyc gene coding for pyruvate carboxylase;
c) the *E. coli* pps gene for phosphoenolpyruvate synthase;
d) the *E. coli* ppc gene coding for phosphoenolpyruvate carboxylase;
e) the *E. coli* genes pntA and pntB coding for transhydrogenase;
f) the *E. coli* rhtB gene imparting homoserine resistance;
g) the *E. coli* mqo gene coding for malate:quinone oxidoreductase;
h) the *E. coli* rhtC gene imparting threonine resistance;
i) the thrE *C. glutamicum* gene coding for the threonine-export protein;
j) the *E. coli* gdhA gene coding for glutamate dehydrogenase;

k) the *E. coli* hns gene coding for the DNA binding protein HLP-II;
l) the *E. coli* pgm gene coding for phosphoglucomutase;
m) the *E. coli* fba gene coding for fructose biphosphate aldolase;
n) the *E. coli* ptsH gene coding for phosphohistidine protein hexose phosphotransferase;
o) the *E. coli* ptsI gene coding for enzyme I of the phosphotransferase system;
p) the *E. coli* crr gene coding for the glucose-specific IIA component;
q) the *E. coli* ptsG gene coding for the glucose-specific IIBC component;
r) the *E. coli* lrp gene coding for the regulator of the leucine regulon;
s) the *E. coli* csrA gene coding for the global regulator Csr;
t) the *E. coli* fadR gene coding for the regulator of the fad regulon;
u) the *E. coli* iclR gene coding for the regulator of central intermediary metabolism;
v) the *E. coli* mopB gene coding for the 10 kDa chaperon;
w) the *E. coli* ahpC gene coding for the small subunit of alkyl hydroperoxide reductase;
x) the *E. coli* ahpF gene coding for the large subunit of alkyl hydroperoxide reductase;
y) the *E. coli* cysK gene coding for cysteine synthase A;
z) the *E. coli* cysB gene coding for the regulator of the cys regulon;
aa) the *E. coli* cysJ gene coding for the flavoprotein of NADPH sulfite reductase;
bb) the *E. coli* cysI gene coding for the haemoprotein of NADPH sulfite reductase;
cc) the *E. coli* cysH gene coding for adenylyl sulfate reductase;
dd) the *E. coli* phoB gene coding for the positive regulator PhoB of the pho regulon;
ee) the *E. coli* phoR gene coding for the sensor protein of the pho regulon;
ff) the *E. coli* phoE gene coding for protein E of the outer cell membrane;
gg) the *E. coli* pykE gene coding for pyruvate kinase I, which is stimulated by fructose;
hh) the *E. coli* pfkB gene coding for 6-phosphofructokinase II;
ii) the *E. coli* malE gene coding for the periplasmic binding protein of maltose transport;
jj) the *E. coli* sodA gene coding for superoxide dismutase;
kk) the *E. coli* rseA gene coding for a membrane protein with anti-sigmaE activity;
ll) the *E. coli* rseC gene coding for a global regulator of the sigmaE factor;
mm) the *E. coli* sucA gene coding for the decarboxylase subunit of 2-ketoglutarate dehydrogenase;
nn) the *E. coli* sucB gene coding for the dihydrolipoyl transsuccinase E2 subunit of 2-ketoglutarate dehydrogenase;
oo) the *E. coli* sucC gene coding for the β-subunit of succinyl-CoA synthetase;
pp) the *E. coli* sucD gene coding for the α-subunit of succinyl-CoA synthetase;
qq) the *E. coli* adk gene coding for adenylate kinase;
rr) the *E. coli* hdeA gene coding for a periplasmic protein with chaperonin-type function;
ss) the *E. coli* hdeB gene coding for a periplasmic protein with chaperonin-type function;
tt) the *E. coli* icd gene coding for isocitrate dehydrogenase;
uu) the *E. coli* mglB gene coding for the periplasmic, galactose-binding transport protein;
vv) the *E. coli* lpd gene coding for dihydrolipoamide dehydrogenase;
ww) the *E. coli* aceE gene coding for the E1 component of the pyruvate-dehydrogenase complex;
xx) the *E. coli* aceF gene coding for the E2 component of the pyruvate-dehydrogenase complex;
yy) the *E. coli* pepB gene coding for aminopeptidase B;
zz) the *E. coli* aldH gene coding for aldehyde dehydrogenase,
aaa) the *E. coli* bfr gene coding for the iron-storage homoprotein;
bbb) the *E. coli* udp gene coding for uridine phosphorylase; and
ccc) the *E. coli* rseB gene coding for the regulator of sigmaE-factor activity.

* * * * *

SEQUENCE LISTING

<160> NUMBER OF SEQ ID NOS: 8

<210> SEQ ID NO 1
<211> LENGTH: 30
<212> TYPE: DNA
<213> ORGANISM: Artificial
<220> FEATURE:
<223> OTHER INFORMATION: PCR Primer
<220> FEATURE:
<221> NAME/KEY: Restriction site
<222> LOCATION: (9)..(14)
<223> OTHER INFORMATION: XbaI site

<400> SEQUENCE: 1

```
gaacaaatct agaaattaag ccggggaggc                                    30
```

<210> SEQ ID NO 2
<211> LENGTH: 24
<212> TYPE: DNA
<213> ORGANISM: Artificial
<220> FEATURE:
<223> OTHER INFORMATION: PCR Primer
<220> FEATURE:
<221> NAME/KEY: Restriction site
<222> LOCATION: (8)..(13)
<223> OTHER INFORMATION: HindIII site

<400> SEQUENCE: 2

```
gctacttaag ctttacaggc tttc                                          24
```

<210> SEQ ID NO 3
<211> LENGTH: 431
<212> TYPE: DNA
<213> ORGANISM: Escherichia coli
<220> FEATURE:
<221> NAME/KEY: yfiD PCR product
<222> LOCATION: (1)..(431)
<223> OTHER INFORMATION:
<220> FEATURE:
<221> NAME/KEY: CDS
<222> LOCATION: (36)..(419)
<223> OTHER INFORMATION: open reading frame yfiD

<400> SEQUENCE: 3

```
gaacaaatct agaaattaag ccggggaggc atcac atg att aca ggt atc cag      53
                                      Met Ile Thr Gly Ile Gln
                                        1               5 att act aaa gcc gct aac gac gat ctg ctg aac tct ttc tgg ctg ctg    101
Ile Thr Lys Ala Ala Asn Asp Asp Leu Leu Asn Ser Phe Trp Leu Leu
         10                  15                  20 gac agc gaa aaa ggc gaa gcg cgt tgc atc gtt gca aaa gca ggt tat    149
Asp Ser Glu Lys Gly Glu Ala Arg Cys Ile Val Ala Lys Ala Gly Tyr
             25                  30                  35 gca gaa gat gaa gtg gtt gca gta agc aaa ctg ggt gac att gaa tac    197
Ala Glu Asp Glu Val Val Ala Val Ser Lys Leu Gly Asp Ile Glu Tyr
     40                  45                  50 cgt gaa gtt cca gta gaa gtg aaa cca gaa gtt cgc gtt gaa ggt ggt    245
Arg Glu Val Pro Val Glu Val Lys Pro Glu Val Arg Val Glu Gly Gly
 55                  60                  65                  70 caa cac ctg aac gtt aac gtt ctg cgt cgc gaa act ctg gaa gat gca    293
Gln His Leu Asn Val Asn Val Leu Arg Arg Glu Thr Leu Glu Asp Ala
                 75                  80                  85 gtt aag cat ccg gaa aaa tat ccg cag ctg acc atc cgt gta tcc ggt    341
Val Lys His Pro Glu Lys Tyr Pro Gln Leu Thr Ile Arg Val Ser Gly
             90                  95                 100
```

```
tat gca gtt cgc ttt aac tct ctg act ccg gaa cag cag cgc gac gtt    389
Tyr Ala Val Arg Phe Asn Ser Leu Thr Pro Glu Gln Gln Arg Asp Val
        105                 110                 115 atc gct cgt acc ttt act gaa agc ctg taa agcttaagta gc              431
Ile Ala Arg Thr Phe Thr Glu Ser Leu
    120                 125
```

<210> SEQ ID NO 4
<211> LENGTH: 127
<212> TYPE: PRT
<213> ORGANISM: Escherichia coli

<400> SEQUENCE: 4

```
Met Ile Thr Gly Ile Gln Ile Thr Lys Ala Ala Asn Asp Asp Leu Leu
1               5                   10                  15

Asn Ser Phe Trp Leu Leu Asp Ser Glu Lys Gly Glu Ala Arg Cys Ile
            20                  25                  30

Val Ala Lys Ala Gly Tyr Ala Glu Asp Glu Val Val Ala Val Ser Lys
        35                  40                  45

Leu Gly Asp Ile Glu Tyr Arg Glu Val Pro Val Glu Val Lys Pro Glu
    50                  55                  60

Val Arg Val Glu Gly Gly Gln His Leu Asn Val Asn Val Leu Arg Arg
65                  70                  75                  80

Glu Thr Leu Glu Asp Ala Val Lys His Pro Gly Lys Tyr Pro Gln Leu
                85                  90                  95

Thr Ile Arg Val Ser Gly Tyr Ala Val Arg Phe Asn Ser Leu Thr Pro
            100                 105                 110

Glu Gln Gln Arg Asp Val Ile Ala Arg Thr Phe Thr Glu Ser Leu
        115                 120                 125
```

<210> SEQ ID NO 5
<211> LENGTH: 28
<212> TYPE: DNA
<213> ORGANISM: Artificial
<220> FEATURE:
<223> OTHER INFORMATION: PCR Primer
<220> FEATURE:
<221> NAME/KEY: Restriction site
<222> LOCATION: (5)..(10)
<223> OTHER INFORMATION: XbaI site

<400> SEQUENCE: 5
ccactctaga aggtaggtgt tacatgtc                                      28

<210> SEQ ID NO 6
<211> LENGTH: 27
<212> TYPE: DNA
<213> ORGANISM: Artificial
<220> FEATURE:
<223> OTHER INFORMATION: PCR Primer
<220> FEATURE:
<221> NAME/KEY: Restriction site
<222> LOCATION: (13)..(18)
<223> OTHER INFORMATION: HindIII site

<400> SEQUENCE: 6
cgatttcagt caaagcttat tacatag                                       27

<210> SEQ ID NO 7
<211> LENGTH: 2325
<212> TYPE: DNA
<213> ORGANISM: Escherichia coli

```
<220> FEATURE:
<221> NAME/KEY: pflB PCR product
<222> LOCATION: (1)..(2325)
<223> OTHER INFORMATION:
<220> FEATURE:
<221> NAME/KEY: CDS
<222> LOCATION: (24)..(2306)
<223> OTHER INFORMATION: pflB coding region

<400> SEQUENCE: 7
ccactctaga aggtaggtgt tac atg tcc gag ctt aat gaa aag tta gcc aca        53
                         Met Ser Glu Leu Asn Glu Lys Leu Ala Thr
                          1               5                  10 gcc tgg gaa ggt ttt acc aaa ggt gac tgg cag aat gaa gta aac gtc         101
Ala Trp Glu Gly Phe Thr Lys Gly Asp Trp Gln Asn Glu Val Asn Val
             15                  20                  25 cgt gac ttc att cag aaa aac tac act ccg tac gag ggt gac gag tcc         149
Arg Asp Phe Ile Gln Lys Asn Tyr Thr Pro Tyr Glu Gly Asp Glu Ser
         30                  35                  40 ttc ctg gct ggc gct act gaa gcg acc acc acc ctg tgg gac aaa gta         197
Phe Leu Ala Gly Ala Thr Glu Ala Thr Thr Thr Leu Trp Asp Lys Val
     45                  50                  55 atg gaa ggc gtt aaa ctg gaa aac cgc act cac gcg cca gtt gac ttt         245
Met Glu Gly Val Lys Leu Glu Asn Arg Thr His Ala Pro Val Asp Phe
 60                  65                  70 gac acc gct gtt gct tcc acc atc acc tct cac gac gct ggc tac atc         293
Asp Thr Ala Val Ala Ser Thr Ile Thr Ser His Asp Ala Gly Tyr Ile
 75                  80                  85                  90 aac aag cag ctt gag aaa atc gtt ggt ctg cag act gaa gct ccg ctg         341
Asn Lys Gln Leu Glu Lys Ile Val Gly Leu Gln Thr Glu Ala Pro Leu
             95                 100                 105 aaa cgt gct ctt atc ccg ttc ggt ggt atc aaa atg atc gaa ggt tcc         389
Lys Arg Ala Leu Ile Pro Phe Gly Gly Ile Lys Met Ile Glu Gly Ser
         110                 115                 120 tgc aaa gcg tac aac cgc gaa ctg gat ccg atg atc aaa aaa atc ttc         437
Cys Lys Ala Tyr Asn Arg Glu Leu Asp Pro Met Ile Lys Lys Ile Phe
     125                 130                 135 act gaa tac cgt aaa act cac aac cag ggc gtg ttc gac gtt tac act         485
Thr Glu Tyr Arg Lys Thr His Asn Gln Gly Val Phe Asp Val Tyr Thr
 140                 145                 150 ccg gac atc ctg cgt tgc cgt aaa tct ggt gtt ctg acc ggt ctg cca         533
Pro Asp Ile Leu Arg Cys Arg Lys Ser Gly Val Leu Thr Gly Leu Pro
155                 160                 165                 170 gat gca tat ggc cgt ggc cgt atc atc ggt gac tac cgt cgc gtt gcg         581
Asp Ala Tyr Gly Arg Gly Arg Ile Ile Gly Asp Tyr Arg Arg Val Ala
             175                 180                 185 ctg tac ggt atc gac tac ctg atg aaa gac aaa ctg gca cag ttc act         629
Leu Tyr Gly Ile Asp Tyr Leu Met Lys Asp Lys Leu Ala Gln Phe Thr
         190                 195                 200 tct ctg cag gct gat ctg gaa aac ggc gta aac ctg gaa cag act atc         677
Ser Leu Gln Ala Asp Leu Glu Asn Gly Val Asn Leu Glu Gln Thr Ile
     205                 210                 215 cgt ctg cgc gaa gaa atc gct gaa cag cac cgc gct ctg ggt cag atg         725
Arg Leu Arg Glu Glu Ile Ala Glu Gln His Arg Ala Leu Gly Gln Met
 220                 225                 230 aaa gaa atg gct gcg aaa tac ggc tac gac atc tct ggt ccg gct acc         773
Lys Glu Met Ala Ala Lys Tyr Gly Tyr Asp Ile Ser Gly Pro Ala Thr
235                 240                 245                 250 aac gct cag gaa gct atc cag tgg act tac ttc ggc tac ctg gct gct         821
Asn Ala Gln Glu Ala Ile Gln Trp Thr Tyr Phe Gly Tyr Leu Ala Ala
             255                 260                 265
```

```
                                                        -continued gtt aag tct cag aac ggt gct gca atg tcc ttc ggt cgt acc tcc acc        869
Val Lys Ser Gln Asn Gly Ala Ala Met Ser Phe Gly Arg Thr Ser Thr
        270                 275                 280 ttc ctg gat gtg tac atc gaa cgt gac ctg aaa gct ggc aag atc acc        917
Phe Leu Asp Val Tyr Ile Glu Arg Asp Leu Lys Ala Gly Lys Ile Thr
285                 290                 295 gaa caa gaa gcg cag gaa atg gtt gac cac ctg gtc atg aaa ctg cgt        965
Glu Gln Glu Ala Gln Glu Met Val Asp His Leu Val Met Lys Leu Arg
    300                 305                 310 atg gtt cgc ttc ctg cgt act ccg gaa tac gat gaa ctg ttc tct ggc       1013
Met Val Arg Phe Leu Arg Thr Pro Glu Tyr Asp Glu Leu Phe Ser Gly
315                 320                 325                 330 gac ccg atc tgg gca acc gaa tct atc ggt ggt atg ggc ctc gac ggt       1061
Asp Pro Ile Trp Ala Thr Glu Ser Ile Gly Gly Met Gly Leu Asp Gly
                335                 340                 345 cgt acc ctg gtt acc aaa aac agc ttc cgt ttc ctg aac acc ctg tac       1109
Arg Thr Leu Val Thr Lys Asn Ser Phe Arg Phe Leu Asn Thr Leu Tyr
            350                 355                 360 acc atg ggt ccg tct ccg gaa ccg aac atg acc att ctg tgg tct gaa       1157
Thr Met Gly Pro Ser Pro Glu Pro Asn Met Thr Ile Leu Trp Ser Glu
        365                 370                 375 aaa ctg ccg ctg aac ttc aag aaa ttc gcc gct aaa gtg tcc atc gac       1205
Lys Leu Pro Leu Asn Phe Lys Lys Phe Ala Ala Lys Val Ser Ile Asp
380                 385                 390 acc tct tct ctg cag tat gag aac gat gac ctg atg cgt ccg gac ttc       1253
Thr Ser Ser Leu Gln Tyr Glu Asn Asp Asp Leu Met Arg Pro Asp Phe
395                 400                 405                 410 aac aac gat gac tac gct att gct tgc tgc gta agc ccg atg atc gtt       1301
Asn Asn Asp Asp Tyr Ala Ile Ala Cys Cys Val Ser Pro Met Ile Val
                415                 420                 425 ggt aaa caa atg cag ttc ttc ggt gcg cgt gca aac ctg gcg aaa acc       1349
Gly Lys Gln Met Gln Phe Phe Gly Ala Arg Ala Asn Leu Ala Lys Thr
            430                 435                 440 atg ctg tac gca atc aac ggc ggt gtt gac gaa aaa ctg aaa atg cag       1397
Met Leu Tyr Ala Ile Asn Gly Gly Val Asp Glu Lys Leu Lys Met Gln
        445                 450                 455 gtt ggt ccg aag tct gaa ccg atc aaa ggc gat gtc ctg aac tat gat       1445
Val Gly Pro Lys Ser Glu Pro Ile Lys Gly Asp Val Leu Asn Tyr Asp
460                 465                 470 gaa gtg atg gag cgc atg gat cac ttc atg gac tgg ctg gct aaa cag       1493
Glu Val Met Glu Arg Met Asp His Phe Met Asp Trp Leu Ala Lys Gln
475                 480                 485                 490 tac atc act gca ctg aac atc atc cac tac atg cac gac aag tac agc       1541
Tyr Ile Thr Ala Leu Asn Ile Ile His Tyr Met His Asp Lys Tyr Ser
                495                 500                 505 tac gaa gcc tct ctg atg gcg ctg cac gac cgt gac gtt atc cgc acc       1589
Tyr Glu Ala Ser Leu Met Ala Leu His Asp Arg Asp Val Ile Arg Thr
            510                 515                 520 atg gcg tgt ggt atc gct ggt ctg tcc gtt gct gct gac tcc ctg tct       1637
Met Ala Cys Gly Ile Ala Gly Leu Ser Val Ala Ala Asp Ser Leu Ser
        525                 530                 535 gca atc aaa tat gcg aaa gtt aaa ccg att cgt gac gaa gac ggt ctg       1685
Ala Ile Lys Tyr Ala Lys Val Lys Pro Ile Arg Asp Glu Asp Gly Leu
540                 545                 550 gct atc gac ttc gaa atc gaa ggc gaa tac ccg cag ttt ggt aac aat       1733
Ala Ile Asp Phe Glu Ile Glu Gly Glu Tyr Pro Gln Phe Gly Asn Asn
555                 560                 565                 570 gat ccg cgt gta gat gac ctg gct gtt gac ctg gta gaa cgt ttc atg       1781
Asp Pro Arg Val Asp Asp Leu Ala Val Asp Leu Val Glu Arg Phe Met
                575                 580                 585
```

-continued

| | |
|---|---|
| aag aaa att cag aaa ctg cac acc tac cgt gac gct atc ccg act cag<br>Lys Lys Ile Gln Lys Leu His Thr Tyr Arg Asp Ala Ile Pro Thr Gln<br>            590                   595                  600 | 1829 |
| tct gtt ctg acc atc act tct aac gtt gtg tat ggt aag aaa acg ggt<br>Ser Val Leu Thr Ile Thr Ser Asn Val Val Tyr Gly Lys Lys Thr Gly<br>        605                   610                   615 | 1877 |
| aac acc cca gac ggt cgt cgt gct ggc gcg ccg ttc gga ccg ggt gct<br>Asn Thr Pro Asp Gly Arg Arg Ala Gly Ala Pro Phe Gly Pro Gly Ala<br>620                   625                   630 | 1925 |
| aac ccg atg cac ggt cgt gac cag aaa ggt gca gta gcc tct ctg act<br>Asn Pro Met His Gly Arg Asp Gln Lys Gly Ala Val Ala Ser Leu Thr<br>635                   640                   645                 650 | 1973 |
| tcc gtt gct aaa ctg ccg ttt gct tac gct aaa gat ggt atc tcc tac<br>Ser Val Ala Lys Leu Pro Phe Ala Tyr Ala Lys Asp Gly Ile Ser Tyr<br>               655                   660                  665 | 2021 |
| acc ttc tct atc gtt ccg aac gca ctg ggt aaa gac gac gaa gtt cgt<br>Thr Phe Ser Ile Val Pro Asn Ala Leu Gly Lys Asp Asp Glu Val Arg<br>            670                   675                   680 | 2069 |
| aag acc aac ctg gct ggt ctg atg gat ggt tac ttc cac cac gaa gca<br>Lys Thr Asn Leu Ala Gly Leu Met Asp Gly Tyr Phe His His Glu Ala<br>               685                   690                  695 | 2117 |
| tcc atc gaa ggt ggt cag cac ctg aac gtt aac gtg atg aac cgt gaa<br>Ser Ile Glu Gly Gly Gln His Leu Asn Val Asn Val Met Asn Arg Glu<br>700                   705                   710 | 2165 |
| atg ctg ctc gac gcg atg gaa aac ccg gaa aaa tat ccg cag ctg acc<br>Met Leu Leu Asp Ala Met Glu Asn Pro Glu Lys Tyr Pro Gln Leu Thr<br>715                   720                   725                 730 | 2213 |
| atc cgt gta tct ggc tac gca gta cgt ttc aac tcg ctg act aaa gaa<br>Ile Arg Val Ser Gly Tyr Ala Val Arg Phe Asn Ser Leu Thr Lys Glu<br>               735                   740                  745 | 2261 |
| cag cag cag gac gtt att act cgt acc ttc act caa tct atg taa<br>Gln Gln Gln Asp Val Ile Thr Arg Thr Phe Thr Gln Ser Met<br>            750                   755                  760 | 2306 |
| taagctttga ctgaaatcg | 2325 |

<210> SEQ ID NO 8
<211> LENGTH: 760
<212> TYPE: PRT
<213> ORGANISM: Escherichia coli

<400> SEQUENCE: 8

Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
        35                  40                  45

Glu Ala Thr Thr Thr Leu Trp Asp Lys Val Met Glu Gly Val Lys Leu
    50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

```
Glu Leu Asp Pro Met Ile Lys Lys Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
        195                 200                 205

Glu Asn Gly Val Asn Leu Glu Gln Thr Ile Arg Leu Arg Glu Glu Ile
    210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
        355                 360                 365

Glu Pro Asn Met Thr Ile Leu Trp Ser Glu Lys Leu Pro Leu Asn Phe
    370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Val Asp Glu Lys Leu Lys Met Gln Val Gly Pro Lys Ser Glu
    450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
            500                 505                 510

Ala Leu His Asp Arg Asp Val Ile Arg Thr Met Ala Cys Gly Ile Ala
        515                 520                 525

Gly Leu Ser Val Ala Ala Asp Ser Leu Ser Ala Ile Lys Tyr Ala Lys
    530                 535                 540
```

-continued

```
Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
            580                 585                 590

His Thr Tyr Arg Asp Ala Ile Pro Thr Gln Ser Val Leu Thr Ile Thr
        595                 600                 605

Ser Asn Val Val Tyr Gly Lys Lys Thr Gly Asn Thr Pro Asp Gly Arg
        610             615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
                645                 650                 655

Phe Ala Tyr Ala Lys Asp Gly Ile Ser Tyr Thr Phe Ser Ile Val Pro
                660                 665                 670

Asn Ala Leu Gly Lys Asp Asp Glu Val Arg Lys Thr Asn Leu Ala Gly
            675                 680                 685

Leu Met Asp Gly Tyr Phe His His Glu Ala Ser Ile Glu Gly Gly Gln
    690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
        755                 760
```